(12) United States Patent
Fu

(10) Patent No.: US 10,540,766 B2
(45) Date of Patent: Jan. 21, 2020

(54) SYSTEMS AND METHODS FOR ARTIFACT CORRECTION OF COMPUTERIZED TOMOGRAPHY

(71) Applicant: SHANGHAI UNITED IMAGING HEALTHCARE CO., LTD., Shanghai (CN)

(72) Inventor: Jianwei Fu, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 0 days.

(21) Appl. No.: 16/018,131

(22) Filed: Jun. 26, 2018

(65) Prior Publication Data

US 2018/0300879 A1  Oct. 18, 2018

Related U.S. Application Data

(63) Continuation of application No. PCT/CN2016/111400, filed on Dec. 22, 2016.

(30) Foreign Application Priority Data

Jan. 30, 2016 (CN) .......................... 2016 1 0068473
Jan. 30, 2016 (CN) .......................... 2016 1 0069409

(51) Int. Cl.
*G06T 7/00* (2017.01)
*A61B 6/03* (2006.01)
*A61B 6/00* (2006.01)

(52) U.S. Cl.
CPC .............. *G06T 7/0014* (2013.01); *A61B 6/03* (2013.01); *A61B 6/505* (2013.01); *G06T 2207/10081* (2013.01); *G06T 2207/30008* (2013.01)

(58) Field of Classification Search
CPC ......... A61B 6/03; A61B 6/5258; A61B 6/505; G06T 7/0014; G06T 2207/10081; G06T 2207/30008

(Continued)

(56) References Cited

U.S. PATENT DOCUMENTS 10,163,206 B2 * 12/2018 Cao ...................... G06T 11/003
2004/0069949 A1   4/2004 Sakaida
(Continued)

FOREIGN PATENT DOCUMENTS

CN     101510298 A     8/2009
CN     102609908 A     7/2012
(Continued)

OTHER PUBLICATIONS

First Office Action in Chinese Application No. 201610069409.8 dated Nov. 30, 2016, 11 pages.

(Continued)

*Primary Examiner* — Daniel G Mariam
(74) *Attorney, Agent, or Firm* — Metis IP LLC

(57) ABSTRACT

A computerized tomography artifact correction method includes: receiving scanning data; reconstructing an image to be corrected and a reference image of the image to be corrected based on the scanning data; determining proportions of a first substance for pixels of the reference image; obtaining a base image of the first substance based on the proportions of the first substance; performing a projection of the base image of the first substance and the reference image to obtain a plurality of projection lines; for each of the plurality of projection lines, obtaining an equivalent length of the first substance corresponding to the projection line and selecting a hardening correction coefficient based on the equivalent length of the first substance corresponding to the projection line; and performing an artifact correction on the (Continued)

image to be corrected based on the hardening correction coefficients.

20 Claims, 12 Drawing Sheets

(58) Field of Classification Search
USPC .......................................................... 382/131
See application file for complete search history.

(56) References Cited

U.S. PATENT DOCUMENTS

| | | |
|---|---|---|
| 2005/0180541 A1 | 8/2005 | Avinash et al. |
| 2006/0159223 A1* | 7/2006 | Wu ..................... A61B 6/032 378/18 |
| 2008/0317315 A1 | 12/2008 | Stemmer |
| 2010/0232725 A1 | 9/2010 | Luijendijk et al. |
| 2011/0142312 A1 | 6/2011 | Toth et al. |
| 2013/0101192 A1 | 4/2013 | Nakanishi et al. |
| 2015/0164456 A1 | 6/2015 | Takamatsu et al. |
| 2016/0110893 A1 | 4/2016 | Pang et al. |

FOREIGN PATENT DOCUMENTS

| | | |
|---|---|---|
| CN | 102768759 A | 11/2012 |
| CN | 103186883 A | 7/2013 |
| CN | 104318536 A | 1/2015 |
| CN | 105608720 A | 5/2016 |
| CN | 105608721 A | 5/2016 |

OTHER PUBLICATIONS

First Office Action in Chinese Application No. 201610068473.4 dated Mar. 30, 2017, 20 pages.
International Search Report in PCT/CN2016/111400 dated Mar. 1, 2017, 4 pages.
Written Opinion in PCT/CN2016/111400 dated Mar. 1, 2017, 5 pages.

* cited by examiner

900

```
Determining theoretical projection values of
water of various thicknesses                    ~910
                    │
                    ▼
Determining ideal projection values of water of
various thicknesses                              ~920
                    │
                    ▼
Determining water hardening correction
coefficients by fitting the theoretical projection
values and the ideal projection values of water  ~930
of various thicknesses
```

```
Selecting a water hardening correction
coefficient based on a thickness of water        ~940
                    │
                    ▼
Correcting the theoretical projection values of
the objects based on the water hardening         ~950
correction coefficient
```

SYSTEMS AND METHODS FOR ARTIFACT CORRECTION OF COMPUTERIZED TOMOGRAPHY

CROSS-REFERENCE OF RELATED APPLICATIONS

This application is a continuation of International Application No. PCT/CN2016/111400, filed on Dec. 22, 2016, which designates the United States of America and claims priority to Chinese Patent Application No. CN 201610069409.8 filed on Jan. 30, 2016 and Chinese Patent Application No. CN 201610068473.4 filed on Jan. 30, 2016, the contents of which are hereby incorporated by reference.

TECHNICAL FIELD

The present disclosure relates to methods and systems for image processing, and in particular, to methods and systems for performing a bone sclerosis artifact correction.

BACKGROUND

Computerized tomography makes use of rays to scan a certain part of a human body taken from a cross section with a certain thickness, and reconstructs cross-sectional images by a computer according to different absorption capacities of different human tissues for rays. During a process for performing a computerized tomography scanning and a reconstruction by using X-rays, the X-rays generated by a ball tube have a certain spectral width, and the X-ray absorption coefficient of a scanning subject decreases as the X-ray energy increases. After the X-rays with continuous energy spectrum pass through a scanning subject, such as a human body, low-energy rays are easily absorbed, high-energy rays are easy to pass through, and the average energy of the rays becomes high and the rays gradually harden. The effect is called as the beam hardening effect. The beam hardening effect may cause artifacts during image reconstruction and affect the quality of the image reconstruction.

SUMMARY

According to an aspect of the present disclosure, a computerized tomography artifact correction method is provided. The method may include: receiving scanning data; reconstructing an image to be corrected and a reference image of the image to be corrected based on the scanning data; determining proportions of a first substance for pixels of the reference image; obtaining a base image of the first substance based on the proportions of the first substance; performing a projection of the base image of the first substance and the reference image to obtain a plurality of projection lines; for each of the plurality of projection lines, obtaining an equivalent length of the first substance corresponding to the projection line and selecting a hardening correction coefficient based on the equivalent length of the first substance corresponding to the projection line; and performing an artifact correction on the image to be corrected based on the hardening correction coefficients.

In some embodiments, the image to be corrected is an image including a bone sclerosis artifact.

In some embodiments, the method further includes reconstructing the image to be corrected based on a first field of view; and reconstructing the reference image based on a second field of view, wherein the second field of view is larger than or equal to the first field of view.

In some embodiments, the method determines a first pixel and a tissue type of the first pixel based on the reference image, and determine the proportion of the first substance based on the tissue type and a CT value of the first pixel.

In some embodiments, the proportion of the first substance reduces as the CT value of the pixel increases.

In some embodiments, the method includes determining a proportion of a second substance for the first pixel.

In some embodiments, the tissue type is bone tissue, the first substance is water, and the second substance is calcium phosphate.

In some embodiments, the method further includes performing a projection of the reference image and the base image of the first substance according to a second channel number and a second projection angle, wherein the reference image is reconstructed according to a first channel number and a first projection angle, the second channel number is less than the first channel number, and the second projection angle is less than the first projection angle.

In some embodiments, the method further includes selecting the hardening correction coefficient from a correction coefficient database based on the equivalent length of the first substance.

In some embodiments, the equivalent length of the first substance is a ratio of a projection value of the base image of the first substance corresponding to the projection line to a CT value of the first substance which the projection line traverses.

In some embodiments, the performing the artifact correction on the image to be corrected based on the hardening correction coefficients includes: obtaining a projection image of the reference image; obtaining an artifact image based on the projection image and the hardening correction coefficients; and subtracting the artifact image from the image to be corrected.

According to an aspect of the present disclosure, a computerized tomography artifact correction method is provided. The method includes determining a bone tissue as an object including a first substance and a second substance; obtaining a theoretical projection value of the bone tissue; performing a hardening correction with respect to the first substance on the theoretical projection value of the bone tissue to obtain a corrected projection value; determining an ideal projection value of the bone tissue; and determining a hardening correction coefficient based on a thickness of the second substance, the ideal projection value of the bone tissue, and the corrected projection value.

In some embodiments, the obtaining the theoretical projection value of the bone tissue and the determining the ideal projection value of the bone tissue includes obtaining scanning data of a phantom.

In some embodiments, the method includes obtaining an equivalent filtration thickness corresponding to a channel through which a measured projection value of the phantom is equal to the theoretical projection value.

In some embodiments, the phantom includes water or organic glass.

In some embodiments, the performing the hardening correction with respect to the first substance on the theoretical projection value includes: determining theoretical projection values and ideal projection values of the first substance of various thicknesses; and determining hardening correction coefficients with respect to the first substance by fitting the theoretical projection values and the ideal projection values.

In some embodiments, the performing a hardening correction with respect to the first substance on the theoretical projection value includes: selecting a hardening correction coefficient with respect to the first substance based on a thickness of the first substance; correcting the theoretical projection value of the bone tissue based on the hardening correction coefficient with respect to the first substance.

In some embodiments, the determining a hardening correction coefficient includes: performing a fitting, wherein an independent variable is a thickness of the second substance, and a dependent variable is a difference between the ideal projection value and the corrected projection value; and obtaining the hardening correction coefficient.

In some embodiments, the determining a hardening correction coefficient includes: performing a fitting, wherein independent variables are the thickness of the first substance and the thickness of the second substance, and a dependent variable is a difference between the ideal projection value and the corrected projection value; and obtaining the hardening correction coefficient.

In some embodiments, the first substance is water and the second substance is a calcium-containing matter.

In some embodiments, the second substance is calcium phosphate.

According to an aspect of the present disclosure, a computerized tomography artifact correction apparatus is provided, including: a correction coefficient determination module configured to determine various objects including a first substance of various thicknesses and a second substance of various thicknesses, determine theoretical projection values and ideal projection values of the objects, determine corrected projection values of the theoretical projection values that are corrected by a hardening correction with respect to the first substance, determine first hardening correction coefficients each of which is based on a thickness of the second substance of an object, the ideal projection value of the object, and the corrected projection value of the theoretical projection value that is corrected by the hardening correction with respect to the first substance; and a correction module configured to reconstruct an image to be corrected and a reference image of the image to be corrected based on the scanning data, select a second hardening correction coefficient from the first hardening correction coefficients by determining an equivalent length of the first substance corresponding to a channel, and correct an artifact of the image to be corrected based on the second hardening correction coefficient.

In some embodiments, the apparatus includes an acquisition module configured to acquire the scanning data of a scanning subject, wherein the correction coefficient determination module is configured to determine the theoretical projection values and the ideal projection values of the objects based on the scanning data.

In some embodiments, the correction coefficient determination module includes: a theoretical projection value unit configured to determine the theoretical projection values of the objects; a first substance hardening correction unit configured to determine the hardening correction coefficient with respect to the first substance; perform a hardening correction with respect to the first substance on the theoretical projection values of the objects based on the hardening correction coefficient with respect to the first substance; and obtain corrected projection values; an ideal projection value unit configured to determine the ideal projection values of the objects; and a hardening correction coefficient determination unit configured to determine the first hardening correction coefficients each of which is based on the thickness of the second substance of an object, the ideal projection value of the object, and the corrected projection value of the theoretical projection value that is corrected by the hardening correction with respect to the first substance.

In some embodiments, the correction module includes: a receiving unit configured to receive the scanning data of the scanning subject; a reconstruction unit configured to reconstruct the image to be corrected according to a first field of view based on the scanning data and reconstruct the reference image of the image to be corrected according to a second field of view based on the scanning data; an assignment unit configured to determine proportions of the first substance for pixels of the reference image; a substance base image unit configured to obtain a water base image of the reference image by multiplying CT values of the pixels by the proportions of the first substance; a projection unit configured to perform a projection of the water base image and the reference image to obtain the equivalent length of the first substance corresponding to a projection line; a correction coefficient determination unit configured to select the second hardening correction coefficient from the first hardening correction coefficients based on the equivalent length of the first substance; an artifact correction unit configured to correct the image to be corrected based on the second hardening correction coefficient.

According to an aspect of the present disclosure, a non-transitory computer readable medium is provided. The non-transitory computer readable medium may include executable instructions. When the executable instructions are executed by at least one processor, the executable instructions may cause the at least one processor to effectuate a method. The method may include: receiving scanning data; reconstructing an image to be corrected and a reference image of the image to be corrected based on the scanning data; determining proportions of a first substance for pixels of the reference image; obtaining a base image of the first substance based on the proportions of the first substance; performing a projection of the base image of the first substance and the reference image to obtain a plurality of projection lines; for each of the plurality of projection lines, obtaining an equivalent length of the first substance corresponding to the projection line and selecting a hardening correction coefficient based on the equivalent length of the first substance corresponding to the projection line; and performing an artifact correction on the image to be corrected based on the hardening correction coefficients.

According to an aspect of the present disclosure, a system is provided. The system may include at least one processor and information. When the information is executed by at least one processor, the information may cause the at least one processor to effectuate a method including: receiving scanning data; reconstructing an image to be corrected and a reference image of the image to be corrected based on the scanning data; determining proportions of a first substance for pixels of the reference image; obtaining a base image of the first substance based on the proportions of the first substance; performing a projection of the base image of the first substance and the reference image to obtain a plurality of projection lines; for each of the plurality of projection lines: obtaining an equivalent length of the first substance corresponding to the projection line; and selecting a hardening correction coefficient based on the equivalent length of the first substance corresponding to the projection line; and performing an artifact correction on the image to be corrected based on the hardening correction coefficients.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below

BRIEF DESCRIPTION OF THE DRAWINGS

The drawings are provided for further understanding of the present disclosure, which constitutes a part of the present disclosure. The exemplary embodiments and the descriptions thereof are provided for the purpose of illustration and not intended to limit the scope of the present disclosure. Like reference numerals in the drawings represent similar structures.

FIG. 9A is an exemplary flowchart of generating a water hardening correction coefficient according to some embodiments of the present disclosure;

FIG. 9B is an exemplary flowchart of performing a water hardening correction based on the water hardening correction coefficient according to some embodiments of the present disclosure;

DETAILED DESCRIPTION

Figure 1:
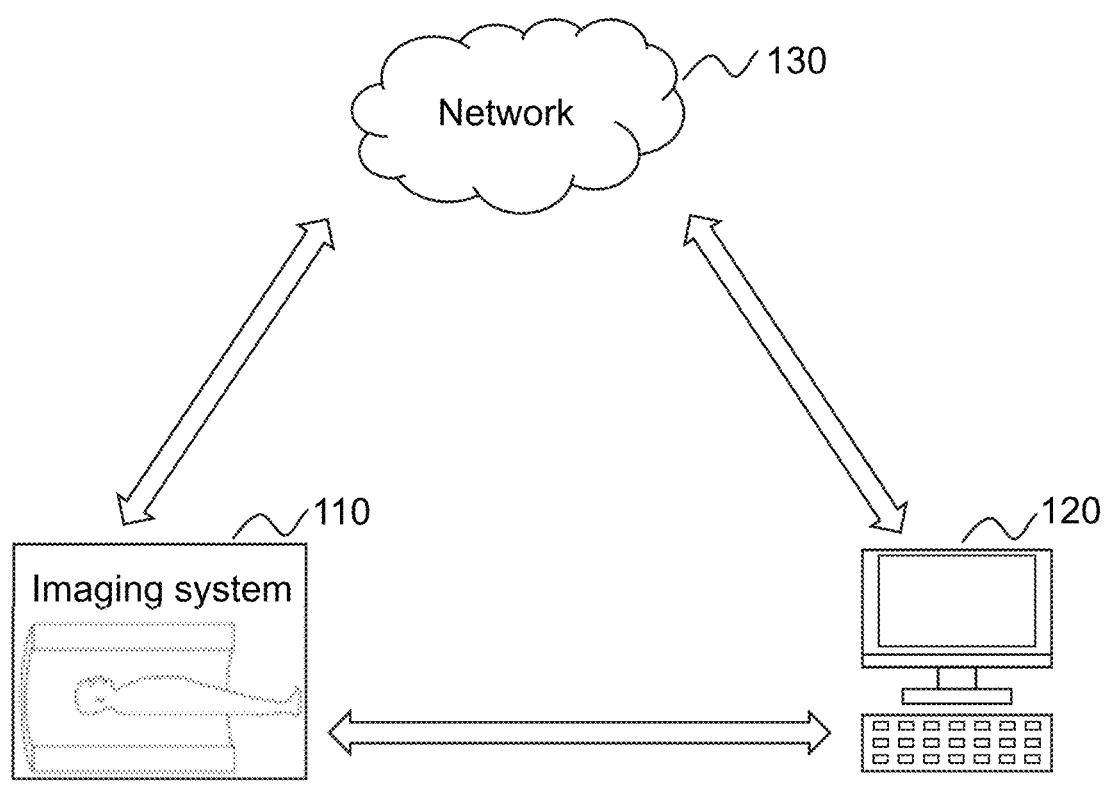
FIG. 1 is a schematic diagram of an image processing system 100 according to some embodiments of the present disclosure.

In order to illustrate the technical solutions related to the embodiments of the present disclosure, brief introduction of the drawings referred to the description of the embodiments is provided below. Obviously, drawing described below are only some examples or embodiments of the present disclosure. Those having ordinary skills in the art, without further creative efforts, may apply the present disclosure to other similar scenarios according to these drawings. Unless stated otherwise or obvious from the context, like reference numerals in the drawings refer to like structures or operations.

As used in the disclosure and the appended claims, the singular forms "a," "an," and "the" include plural referents unless the content clearly dictates otherwise. It will be further understood that the terms "comprise," "comprising," "include," and/or "including" when used in the disclosure, specify the presence of stated operations and elements, but do not preclude the presence or addition of one or more other operations and elements.

Some modules of the system may be referred to in various ways according to some embodiments of the present disclosure, however, any number of different modules may be used and operated in an imaging system and/or a processor. These modules are intended to be illustrative, not intended to limit the scope of the present disclosure. Different modules may be used in different aspects of the system and method.

According to some embodiments of the present disclosure, flow charts are used to illustrate the operations performed by the system. It is to be expressly understood, the operations above or below may or may not be implemented in order. Conversely, the operations may be performed in inverted order, or simultaneously. Besides, one or more other operations may be added to the flowcharts, or one or more operations may be omitted from the flowchart.

FIG. 1 is a schematic diagram of an image processing system 100 according to some embodiments of the present disclosure. The image processing system 100 may include an imaging system 110, a processing device 120, and a network 130. In some embodiments, the imaging system 110 may be a single mode imaging device or a multi-modality imaging system. In some embodiments, the processing device 120 may process acquired image data to obtain images and/or related information.

The imaging system 110 may be a single imaging system or a combination of a plurality of various imaging systems. The imaging system may perform an imaging operation by scanning a target. In some embodiments, the imaging system may be a medical imaging system. The medical imaging system may acquire image information of various parts of a human body. The medical imaging system may be an X-ray C-arm system, an integral medical imaging system, etc.

The imaging system 110 may include one or more scanners. The scanner may be a digital subtraction angiography (DSA), a magnetic resonance angiography (MRA), a computerized tomography angiography (CTA), a positron emission computerized tomography scanner (PET Scanner), a single photon emission computerized tomography scanner (SPECT Scanner), a computerized tomography scanner (CT Scanner), a magnetic resonance imaging scanner (MRI Scanner), a digital radiography scanner (DR Scanner), a multi-modality scanner, or the like, or any combination thereof. In some embodiments, the multi-modality scanner may be a computerized tomography-positron emission tomography scanner (CT-PET scanner), a computerized tomography-magnetic resonance imaging scanner (CT-MRI scanner), a positron emission tomography-magnetic resonance imaging scanner (PET-MRI scanner), a digital subtraction angiography-magnetic resonance imaging scanner (DSA-MRI Scanner), etc.

The processing device 120 may process acquired data information. In some embodiments, the data information may include text information, image information, sound information, or the like, or any combination thereof. In some embodiments, the processing device 120 may include a processor, a processing core, one or more storage devices, or the like, or any combination thereof. For example, the processing device 120 may include a central processing unit (CPU), an application-specific integrated circuit (ASIC), an application-specific instruction-set processor (ASIP), and a graphics processing unit (GPU), a physical processing unit (PPU), a digital signal processor (DSP), a field programmable gate array (FPGA), a programmable logic device (PLD), a controller, a microcontroller unit, a processor, a microprocessor, an advanced RISC machine processor, or the like, or any combination thereof. In some embodiments, the processing device 120 may process image information obtained from the imaging system 110.

The network 130 may be a single network or a combination of a plurality of various networks. For example, the network 130 may be a local area network (LAN), a wide area network (WAN), a public network, a private network, a proprietary network, a public switched telephone network (PSTN), the Internet, a wireless network, a virtual network, a metropolitan area network, a telephone network, or the like, or any combination thereof. The network 130 may include a plurality of network access points, for example, wired or wireless access points such as wired access points, wireless access points, base stations, Internet exchange points, etc. Through these access points, a data source may access the network 130 and transmit data information via the network 130. For the convenience of understanding, the imaging system 110 in medical image processing is described as an example, but the present disclosure is not limited to the scope of the embodiment. For example, the imaging system 110 may be a computerized tomography (CT) imaging system, the network 130 of the processing device 120 may be classified into a wireless network (Bluetooth, a wireless local area network (WLAN, Wi-Fi, WiMax, etc.), a mobile network (2G, 3G, 4G signals, etc.), or other connection modes (a virtual private network (VPN), a shared network, near field communication (NFC), ZigBee, etc.). In some embodiments, the network 130 may be used for communication of the processing device 120, receiving internal or external information of the processing device 120, and transmitting information to other internal parts or external parts of the processing device 120.

It should be noted that the processing device 120 may actually exist in the imaging system 110 or perform corresponding functions through a cloud computing platform. The cloud computing platform may include a storage cloud platform mainly for data storage, a computing cloud platform mainly for data processing, and a comprehensive cloud computing platform both for data storage and processing. The cloud platform used by the imaging system 110 may be a public cloud, a private cloud, a community cloud, a hybrid cloud, etc. For example, according to actual needs, some image information and/or data information output by the imaging system 110 may be calculated and/or stored by a user cloud platform. Other image information and/or data information may be calculated and/or stored by the local processing device 120.

It should be noted that the above description of the image processing system is merely provided for the purpose of illustration, and is not intended to limit the present disclosure to the scope of the embodiments. It should be understood that, for those skilled in the art, after understanding the principle of the system, it may be possible to combine the modules, connect a subsystem which is constituted by the modules with other modules, and make various modifications and changes to the configuration of the image processing system without departing from the principle. However, these modifications and changes do not depart from the scope of the above description.

Figure 2:
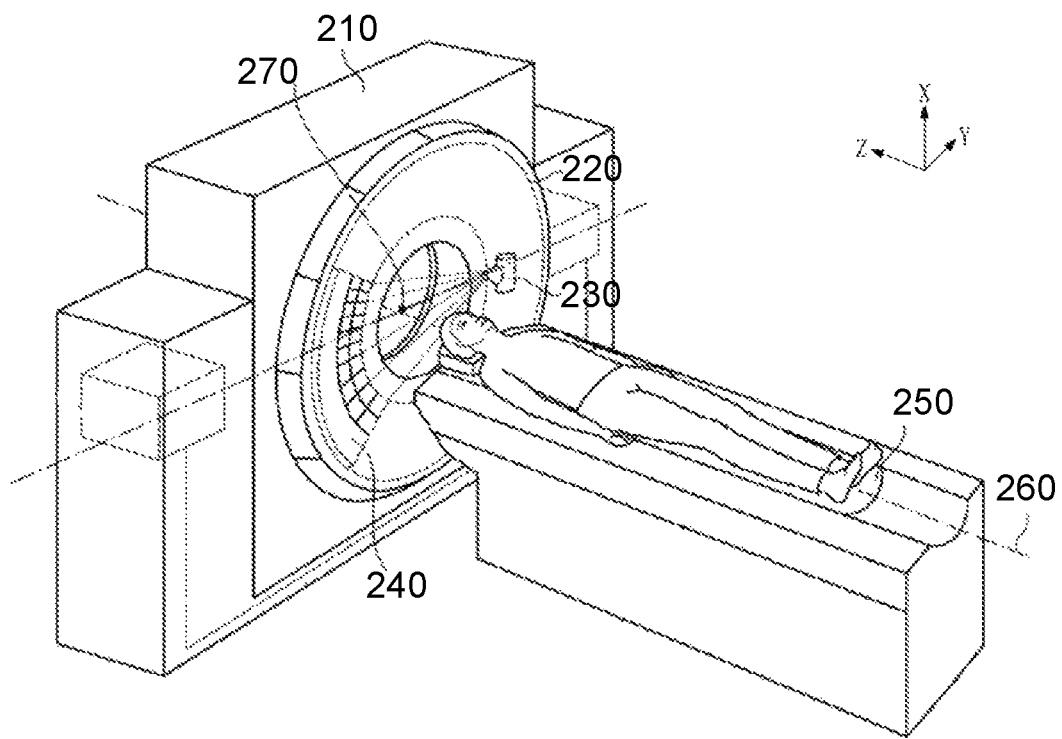
FIG. 2 is a schematic diagram of a computerized tomography imaging system 200 according to some embodiments of the present disclosure.

FIG. 2 is a schematic diagram of a computerized tomography imaging system 200 according to some embodiments of the present disclosure. The imaging system 200 may be a specific embodiment of the imaging system 110. The imaging system 200 may include a gantry 210 and an examination table 250.

In some embodiments, the gantry 210 may include a rotatable portion 220 which rotates around an axis of the imaging system 200. A spatial structure of the rotatable portion 220 may be a cylinder, an ellipsoid, a cuboid, or the like, or any combination thereof. In some embodiments, the rotatable portion 220 may include an X-ray source 230, an X-ray detector 240, and a scanning chamber 270. The rotatable portion 220 may rotate around an axis 260 of the imaging system 200. The X-ray source 230 and the X-ray detector 240 may rotate around the axis 260 along with the rotatable portion 220.

When an examination is performed, a subject (e.g., a patient, a phantom, etc.) may be placed on the examination table 250. The examination table 250 may be pushed into the scanning chamber 270 along a Z-axis direction. The X-ray source 230 and the X-ray detector 240 may acquire scanning data of the patient when rotating around the axis 260. The scanning data may be used to reconstruct, for example, an image to be corrected, a reference image of the image to be corrected, etc.

In some embodiments, the imaging system 200 may perform a helical scanning. During the helical scanning, the scanning subject may be moved back and forth along the axis 260 while the X-ray source may rotate around the axis 260. The X-ray source may produce a helical trajectory relative to the subject.

Figure 3:
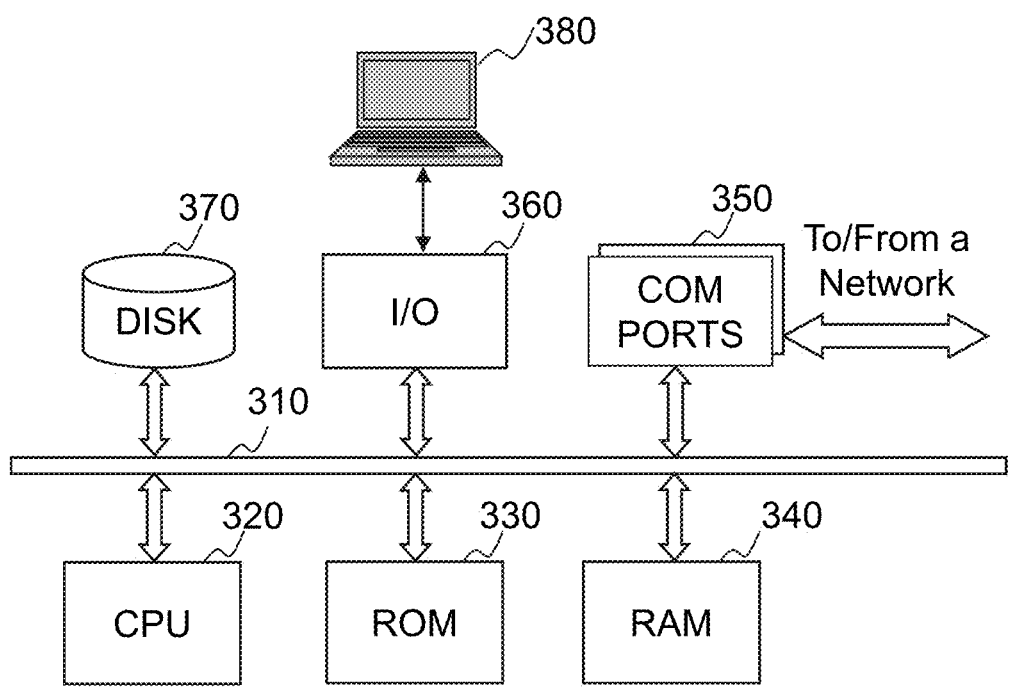
FIG. 3 is a schematic diagram of a computer device configuration of an processing device 120 according to some embodiments of the present disclosure.

FIG. 3 is a schematic diagram of a computer device configuration of the processing device 120 according to some embodiments of the present disclosure. A computer 300 may be used to implement a specific system disclosed in the present disclosure. The specific system in the embodiment explains a hardware platform including a user interface by using a functional block diagram. The computer 300 may implement one or more components, modules, units, sub-units of the processing device 120. In addition, the processing device 120 may be implemented by the computer 300 through hardware devices, software programs, firmware, and a combination thereof. The computer may be a general purpose computer or a special purpose computer, both may be used to implement a specific system in the embodiment. For convenience, only one computer is shown in FIG. 3, but related computer functions described in the embodiment to provide information required for image processing may be implemented in a distributed fashion on a number of similar platforms, to distribute the processing load.

As shown in FIG. 3, the computer 300 may include an internal communication bus 310, a processor 320, a read only memory (ROM) 330, a random access memory (RAM) 340, a communication port 350, an input/output component 360, a disk 370, and a user interface 380. The internal communication bus 310 may implement data communication among the components of the computer 300. The processor 320 may execute program instructions to perform any of functions, components, modules, units, sub-units of the processing device 120 described herein. The processor 320 may include one or more processors. The communication port 350 may implement data communication (e.g., via the network 130) between the computer 300 and other components (e.g., the imaging system 110) of the system 100. The computer 300 may also include program storage units and data storage units of various forms, such as the disk 370, the ROM 330, the RAM 340, for storing various data files used in computer processing and/or communication and possible program instructions executed by the processor 320. The input/output component 360 may support an input/output data flow between the computer 300 and other components (e.g., the imaging system 110) of the system 100. The computer 300 may also transmit and receive information and data from the network 130 via the communication port 350.

Those skilled in the art may understand that various variations and improvements of the contents disclosed in the present disclosure may be made. For example, the various system components described above are implemented by hardware devices, but may also be implemented by only software solutions. For example, a system may be installed in an existing server. In addition, location information disclosed herein may be provided through a firmware, a combination of firmware and software, a combination of firmware and hardware, or a combination of hardware, firmware, and software.

The above description is merely a specific embodiment of the present disclosure and should not be considered as the only embodiment. It will be apparent to those skilled in the art that, after understanding the contents and the principles of the present disclosure, various modifications and changes may be made in the form and detail without departing from the principles and structures of the present disclosure. However, these modifications and changes are still within the scope of the claims of the present disclosure.

Figure 4:
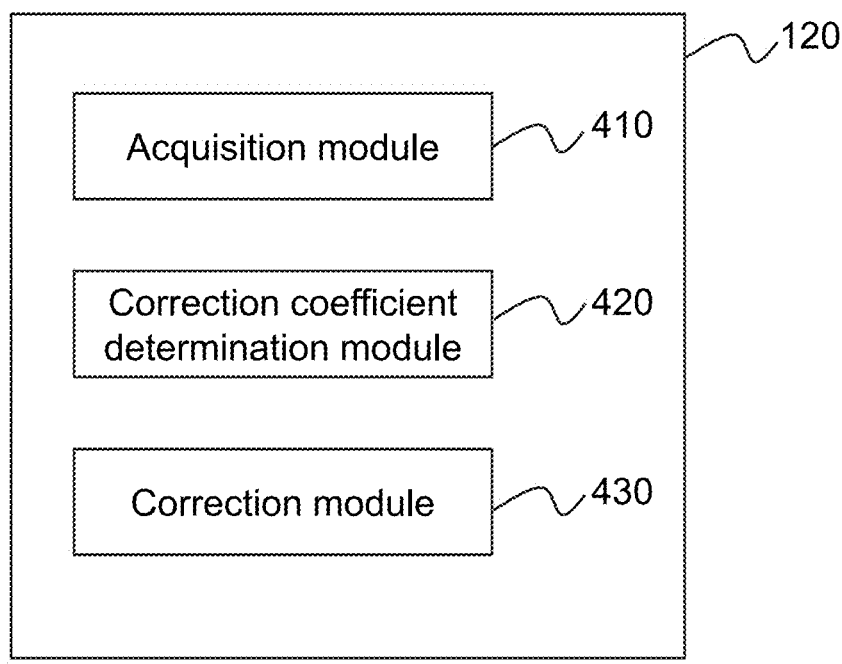
FIG. 4 is a schematic diagram of modules in the processing device 120 according to some embodiments of the present disclosure.

FIG. 4 is a schematic diagram of modules in the processing device 120 according to some embodiments of the present disclosure. The processing device 120 may include an acquisition module 410, a correction coefficient determination module 420, and a correction module 430. The connection among the modules of the processing device 120 may be a wired connection, a wireless connection, or a combination thereof. Each module of the processing device 120 may be local, remote, or a combination thereof. The correspondence relationship among the modules of the processing device 120 may be one-to-one, one-to-many, or many-to-many. For example, the processing device 120 may include one acquisition module 410 and one correction coefficient determination module 420. As another example, the processing device 120 may include a plurality of acquisition modules 410 and a plurality of correction coefficient determination modules 420. The plurality of correction coefficient determination modules 420 may correspond to the plurality of acquisition modules 410 respectively, and each of the plurality of correction coefficient determination modules 420 may process the image data from the corresponding acquisition module 410 accordingly.

The acquisition module 410 may acquire scanning data of a scanning subject. In some embodiments, the imaging system 200 may reconstruct an image to be corrected and a reference image of the image to be corrected by the processing device 120 based on the scanning data, and perform a subsequent artifact correction. In some embodiments, the scanning data may refer to parameters associated with the X-rays passing through the scanning subject which may be acquired by a detector (e.g., the detector 240 illustrated in FIG. 2). The parameters associated with the X-rays may be intensity, a frequency, a wavelength, or the like, or any combination thereof. The acquisition module 410 may transmit the acquired scanning data to the correction coefficient determination module 420.

In some embodiments, the acquisition module 410 may determine an equivalent filtration thickness of the imaging system 110 based on scanning data of a phantom. The equivalent filtration thickness may represent X-ray hardening during transmission of X-rays from a radiation source to the scanning subject or a region of interest of the scanning subject. The hardening may refer to a phenomenon that low-energy photons are more easily absorbed by the phantom when X-rays pass through the phantom. The correction coefficient determination module 420 may generate a hardening correction coefficient based on the equivalent filtration thickness.

The correction coefficient determination module 420 may determine a theoretical projection value and an ideal projection value of an object. The object may include a first substance and a second substance. In some examples, the first substance may be water. In some examples, the second substance may be a calcium-containing substance. For example, the calcium-containing material may be calcium phosphate. In some examples, a calcium content of the calcium-containing material is relatively high, for example, the calcium content is 20%, 25%, 35%, etc.

It should be noted that the above description of the first substance and the second substance is merely provided for the purpose of illustration, and is not intended to limit the present disclosure to the scope of the embodiment. It may be understood that for those skilled in the art, the selection range of the first substance and the second substance is not limited to the embodiment. The following description takes the first substance being water and the second substance being calcium phosphate as an example. The systems and methods described in the present disclosure may also be applied to other substances or a combination of substances.

When a computerized tomography is performed on a scanning subject (e.g., a phantom), a measured projection value represents a projection value of the scanning subject actually detected by the detector 240; a theoretical projection value represents a calculated projection value of the scanning subject with a distribution of X-ray photon energies into consideration; and an ideal projection value represents a projection value under an assumption that all photon energies of X-rays that pass through the subject are E0 (E0 is an adjustable parameter which represents that an energy of a single photon is E0). In some embodiments, the measured projection value may be expressed by the formula below:

$$ProjMeas = -\log\left(\frac{I}{I_0}\right) \qquad (1)$$

In formula (1), $I_0$ may represent the intensity of X-rays incident on the scanning subject and I may represent the intensity of X-rays projected out of the subject.

The correction coefficient determination module 420 may further perform a water hardening correction on the theoretical projection value to obtain a water hardening corrected projection value (referred to as "hardening corrected projection value" for short). The correction coefficient determination module 420 may generate a hardening correction coefficient based on a thickness of water, a thickness of calcium phosphate, a hardening corrected projection value of an object including water and calcium phosphate, and/or an ideal projection value of the object. The water hardening correction is described elsewhere in the present disclosure (e.g., FIG. 9A, FIG. 9B, and the description thereof).

The correction coefficient determination module 420 may determine a hardening correction coefficient of an object. A correction coefficient database may include a plurality of hardening correction coefficients. In some embodiments, for a channel, the correction coefficient determination module 420 may determine a hardening corrected projection value and an ideal projection value of an object. The correction coefficient determination module 420 may perform fitting on the above parameters to determine a hardening correction coefficient. The channel is described elsewhere in the present disclosure, for example, FIG. 13 and the description thereof. The above parameters may include the thickness of water in the object, the thickness of calcium phosphate in the object, the hardening corrected projection value of the object, and the ideal projection value of the object.

Take an object including water and calcium phosphate as an example. A channel may correspond to a plurality of objects. Each of the plurality of objects includes water and calcium phosphate, and thickness proportions of water and calcium phosphate are different; the correction coefficient determination module 420 may determine a hardening correction coefficient for each of the objects to generate a correction coefficient database. For example, the plurality of objects may be divided into several groups; thicknesses of water in objects belonging to a same group are the same, and thicknesses of calcium phosphate are different (e.g., the thicknesses of calcium phosphate traverse a range); thicknesses of water in objects belonging to different groups are different. The correction coefficient determination module 420 may determine a hardening correction coefficient for each of a plurality of objects corresponding to the channel to obtain hardening correction coefficients of a plurality of objects corresponding to a plurality of combinations of thickness of water and thicknesses of calcium phosphate, and generate a correction coefficient database. The correction coefficient database is described elsewhere in the application, for example, FIG. 10 and the description thereof.

The correction module 430 may determine a parameter based on the scanning data acquired by the acquisition module 410. The scanning data received by the correction module 430 may be the same as or different from the scanning data received by the correction coefficient determination module 420 from the acquisition module 410. For example, the scanning data received by the correction coefficient determination module 420 may be scanning data of a phantom, and the scanning data received by the correction module 430 may be scanning data of a patient or a human body. In some embodiments, the parameter determined by the correction module 430 may be an equivalent length of water, an equivalent length of calcium phosphate, the intensity of X-rays that passed through the scanning subject, or the like, or any combination thereof. The equivalent length of a substance is described elsewhere in the present disclosure, for example, FIG. 10 and the description thereof.

In some embodiments, the correction module 430 may select a corresponding hardening correction coefficient from the correction coefficient database based on the parameter. The correction module 430 may perform an artifact correction on an image to be corrected based on the selected hardening correction coefficient. In some embodiments, the correction module 430 may generate an artifact image. The correction module 430 may remove the artifact image from the image to be corrected. The correction module 430 may obtain a corrected image, realizing an artifact correction.

In some embodiments, the correction module 430 may determine a distribution of substance components included in the object based on the scanning data acquired by the acquisition module 410. The correction module 430 may determine an effect of the distribution of the substance components on the image. The correction module 430 may correct the image to be corrected based on the effect to obtain a corrected image.

Figure 5:
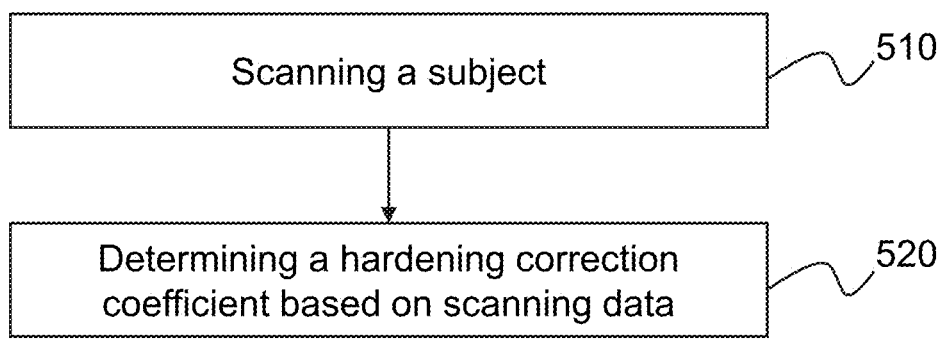
FIG. 5 is an exemplary flowchart of generating a correction coefficient database according to some embodiments of the present disclosure.

FIG. 5 is a schematic flowchart of generating a correction coefficient database according to some embodiments of the present disclosure. In 510, a scanning subject may be scanned by the processing device 120. The scanning subject may include a phantom. In some embodiments, a thickness and a material of the phantom may be known. In some embodiments, the phantom may include a material similar to human soft tissue. The material may be water, organic glass, etc. The human soft tissue may include water, tendon, ligament, muscle, nerve, etc. The material used for manufacturing the phantom may be pure. The phantom may be a cylinder. In some embodiments, the phantom may be a cylindrical phantom made of organic glass. In some embodiments, the wall of the phantom may be a cylindrical barrel made of organic glass and the interior of the phantom is filled with water. In some embodiments, X-ray attenuation characteristics of the material of the phantom may be similar to that of the human soft tissue. In some embodiments, a size of the phantom may be a typical size of a human head. In some embodiments, a plurality of phantoms may be used to cover a certain range. The length of the range may be tens to hundreds of millimeters. The plurality of phantoms may include a cuboid, a cube, an ellipsoid, a cylinder, or the like, or any combination thereof.

In 520, the correction coefficient database may be generated by the processing device 120. The processing device 120 may generate the correction coefficient database based on the scanning data acquired in 510. In some embodiments, a projection value of an object may be determined by the processing device 120 in 520. In some embodiments, the object may include water and calcium phosphate. In an object, a thickness of water and a thickness of calcium phosphate may be the same or different. Two different objects may differ in an overall size, and/or a size of a water containing portion, and/or a size of a calcium phosphate containing portion, etc. The projection value of the object may include a theoretical projection value, an ideal projection value, a measured projection value, a hardening corrected projection value, or the like, or any combination thereof.

In X-ray scanning, according to the base material decomposition theory, a linear attenuation coefficient of an object including a first substance and a second substance may be a linear combination of mass attenuation coefficients of the first substance and the second substance. A linear attenuation coefficient of an object may represent a relationship between the intensity of the X-rays incident on the object and intensity of the X-rays projected out of the object. The linear attenuation coefficient of an object may be associated with a parameter (e.g., a thickness, an area, a shape, etc.) of the object. In some embodiments, the object including the first substance and the second substance may be a human tissue, a bone tissue, a soft tissue, a head support/bed plate, etc. The bone tissue may include water and a calcium-containing substance, for example, calcium phosphate.

In 520, the processing device 120 may generate a hardening correction coefficient based on a thickness of water, a thickness of calcium phosphate, a hardening corrected projection value of an object of a thickness, and/or an ideal projection value of the object of the thickness. The thickness of the object may be determined based on a thickness of water and a thickness of calcium phosphate.

In some embodiments, in 520, the processing device 120 may determine hardening corrected projection values and ideal projection values of different objects. The objects may be divided into one or more groups; thicknesses of water of objects belonging to a same group are the same and thicknesses of calcium phosphate are different (e.g., the thicknesses of calcium phosphate traverse a range); thicknesses of water of objects belonging to different groups are different. It should be understood that grouping the objects herein is performed for the convenience of describing differences among different objects in some embodiments. In 520, the processing device 120 may perform fitting on the parameters to generate a hardening correction coefficient and generate the correction coefficient database. The parameters may include the thickness of water, the thickness of calcium phosphate, the hardening corrected projection value of the object, and the ideal projection value of the object. The correction coefficient database is described elsewhere in the present disclosure, for example, FIG. 10 and the description thereof.

Figure 6:
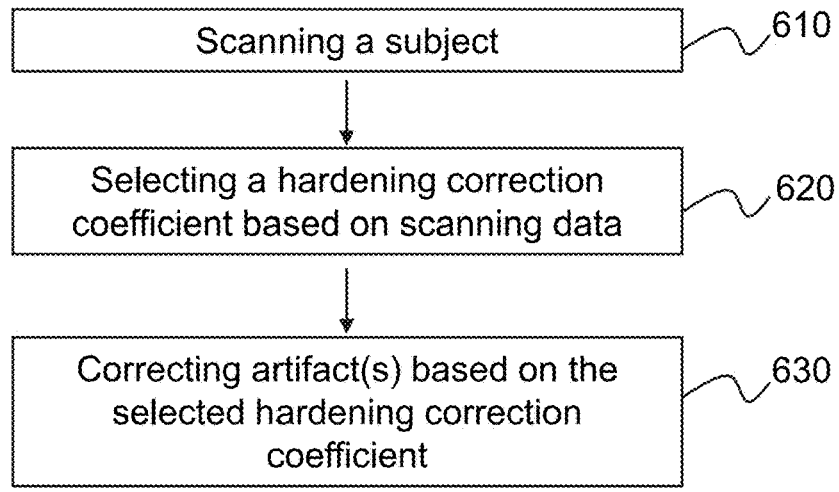
FIG. 6 is an exemplary flowchart of performing an artifact correction according to some embodiments of the present disclosure.

FIG. 6 is a schematic flowchart of performing an artifact correction according to some embodiments of the present disclosure. In 610, a scanning subject may be scanned by the processing device 120 to acquire scanning data. The subject may include a patient, etc. When the imaging system 200 scans the subject, bone sclerosis artifacts may occur due to the beam hardening effect.

In some embodiments, a human tissue may include one or more base materials. For example, when the human tissue includes two base materials, one base material may be called as a first substance and the other base material may be called as a second substance. In some embodiments, the first substance may be close to a soft tissue, such as water; the second substance may be close to a bone tissue, such as calcium phosphate. A proportion of a base material may be determined based on a type of a tissue to which the base material belongs and/or CT values of image pixels. In X-ray scanning, according to the base material decomposition theory, a linear attenuation coefficient of an object including a first substance and a second substance may be a linear combination of mass attenuation coefficients of the first substance and the second substance. In some embodiments, the object may be a human tissue (e.g., a bone tissue, a soft tissue, etc.), a head support/bed plate, etc.

In 620, the processing device 120 may select a hardening correction coefficient based on the scanning data. The processing device 120 may receive the scanning data. The scanning data may be real-time data obtained by scanning a subject by an imaging device or scanning data acquired from a storage device. The processing device 120 may reconstruct, for example, an image to be corrected based on the scanning data. The image to be corrected may be an original image including artifact(s) reconstructed by the processing device 120 according to a first field of view based on the scanning data. The first field of view may be a field of view set by a user. In some embodiments, the processing device 120 may generate a reference image of the image to be corrected. The processing device 120 may perform a re-reconstruction according to a second field of view based on the scanning data to obtain the reference image of the image to be corrected. The second field of view may be larger than or equal to the first field of view (e.g., a field of view set by a user). The second field of view may be set to ensure that the reference image includes all scanned portions of the scanning subject in the first field of view.

In some embodiments, in 620, the processing device 120 may determine proportions of water for the reference image and obtain a water base image based on the proportions of water. The processing device 120 may perform a projection operation of the water base image and the reference image to obtain an equivalent length of water corresponding to each projection line of the projection operation. According to the equivalent length of water, the processing device 120 may select a hardening correction coefficient from the hardening correction coefficients which have been generated. For example, the processing device 120 may search for a corresponding hardening correction coefficient from the correction coefficient database based on a channel index number of a channel and an equivalent length of water corresponding to the channel. The equivalent length of an object is described elsewhere in the present disclosure, for example, FIG. 10 and the description thereof. The channel index number is described elsewhere in the present disclosure, for example, FIG. 11 and the description thereof.

In 630, the processing device 120 may perform an artifact correction based on the selected hardening correction coefficient. In 630, an artifact image may be obtained by the correction module 430. The processing device 120 removes the artifact image from the image to be corrected to obtain a corrected image. The image to be corrected may be an original image including artifact(s) reconstructed by the processing device 120 according to a first field of view based on the scanning data. The first field of view may be a field of view set by a user.

Figure 7:
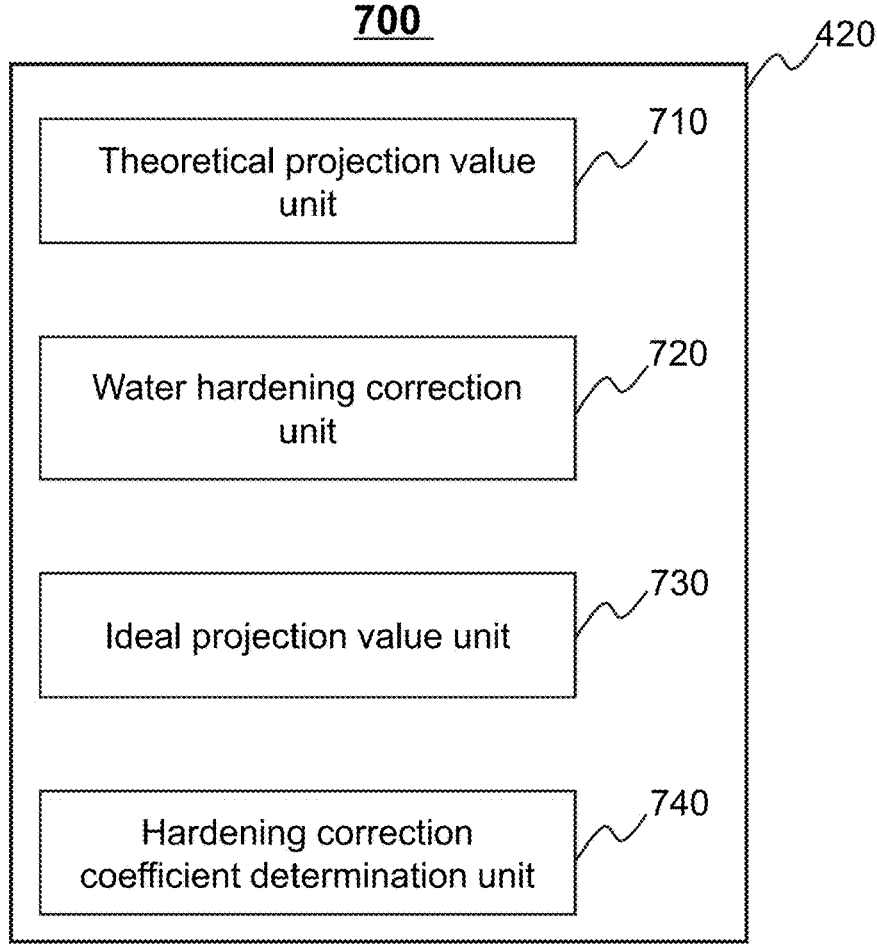
FIG. 7 is a schematic diagram of a correction coefficient determination module 420 in the processing device 120 according to some embodiments of the present disclosure.

FIG. 7 is a schematic diagram of a correction coefficient determination module 420 in the processing device 120 according to some embodiments of the present disclosure. The correction coefficient determination module 420 may include the following units: a theoretical projection value unit 710, a water hardening correction unit 720, an ideal projection value unit 730, and a hardening correction coefficient determination unit 740. It should be noted that the above description of the structure of the correction coefficient determination module 420 in the processing device 120 is merely exemplary and is not intended to limit the present disclosure to the scope of the embodiment. In some embodiments, the correction coefficient determination module 420 may also include other units. In some embodiments, some of the above units may be unnecessary. In some embodiments, some of the above units may be combined into a single unit for cooperation. In some embodiments, the above units may be independent. "The units may be independent" may refer to that each unit executes a respective function. In some embodiments, the above units may be interrelated. "The units may be interrelated" may refer to that data in each unit may be cross used.

The theoretical projection value unit 710 may determine theoretical projection values ProjCal of different objects. As an example, a theoretical projection value ProjCal of an object may be determined according to formula (2) below:

$$ProjCal = -\log\left(\frac{\int S(E) \cdot \exp[-\mu_{filter}(E) \cdot L_{filter}] \cdot \exp[-\mu_{phan}(E) \cdot L_{phan}] \cdot D(E) \cdot dE}{\int S(E) \cdot \exp[-\mu_{filter}(E) \cdot L_{filter}] \cdot D(E) \cdot dE}\right) \quad (2)$$

In formula (2), E may represent X-ray photon energy, S(E) may be an X-ray spectrum emitted by the ball tube, D(E) may be a detector response of the imaging system 110, $\mu_{filter}(E)$ may be a linear attenuation coefficient of an equivalent filtration material, $\mu_{phan}(E)$ may be a linear attenuation coefficient of a scanning subject, $L_{filter}$ may be an equivalent filtration thickness corresponding to a detection unit, and $L_{phan}$ may be a thickness of the scanning subject. In some embodiments, a detection unit may correspond to a channel. In the present disclosure, the same physical symbols represent the same physical meaning unless otherwise specified.

In some embodiments, the equivalent filtration thickness $L_{filter}$ may be an equivalent filtration thickness corresponding to a channel through which the measured projection value and the theoretical projection value of the scanning subject are equal within an allowable error range. The theoretical projection value unit 710 may determine the equivalent filtration thickness $L_{filter}$ based on an iterative method. For example, the theoretical projection value unit 710 may iteratively modify the equivalent filtration thickness $L_{filter}$ in formula (2) and calculate a corresponding theoretical projection value until the theoretical projection value is equal to the measured projection value.

In some embodiments, the object may include water and calcium phosphate. The theoretical projection values ProjCal$_{i,j}$ of different objects may be represented by the formula below:

$$ProjCal_{i,j} = -\log\left(\frac{\int S(E) \cdot \exp[-\mu_{filter}(E) \cdot L_{filter}] \cdot \exp[-\mu_{H_2O}(E) \cdot L_{H_2O,i}] \cdot \exp[-\mu_{phospca}(E) \cdot L_{phospca,j}] \cdot D(E) \cdot dE}{\int S(E) \cdot \exp[-\mu_{filter}(E) \cdot L_{filter}] \cdot D(E) \cdot dE}\right) \quad (3)$$

$\mu_{H_2O}(E)$ may represent a linear attenuation coefficient of water, and $L_{H_2O,i}$ (i=0, 1, 2, . . . ) may represent a thickness of water, wherein different i may correspond to different thicknesses of water. $\mu_{phospca}(E)$ may represent a linear attenuation coefficient of calcium phosphate, $L_{phospca,j}$ (j=0, 1, 2, . . . ) may represent a thickness of calcium phosphate, wherein different j may correspond to different thicknesses of calcium phosphate.

The water hardening correction unit 720 may generate a water hardening correction coefficient. In some embodiments, the water hardening correction unit 720 may select the water hardening correction coefficient from the generated water hardening correction coefficients based on a thickness of water. The water hardening correction unit 720 may further correct theoretical projection values ProjCal$_{i,j}$ of different objects based on the selected water hardening correction coefficient and obtain hardening corrected projection values ProjCorrected$_{i,j}$. The water hardening correction is described elsewhere in the present disclosure, for example, FIG. 9A, FIG. 9B, and the descriptions thereof.

The ideal projection value unit 730 may determine ideal projection values of different objects. The object may include water and calcium phosphate. The objects may be divided into one or more groups; thicknesses of water of objects belonging to a same group are the same and thicknesses of calcium phosphate are different (e.g., the thicknesses of calcium phosphate traverse a range); thicknesses of water of objects belonging to different groups are different. It should be understood that grouping the objects herein is performed for the convenience of describing differences among different objects in some embodiments. The ideal projection values ProjCal$_{i,j}$ may be determined according to the formula below:

$$ProjIdeal_{i,j} = \mu_{H_2O}(E_0) \cdot L_{H_2O,i} + \mu_{phospca}(E_0) \cdot L_{phospca,j} \quad (4)$$

In formula (4), $\mu_{H_2O}(E_0)$ may represent a linear attenuation coefficient of water with respect to X-rays in which all photon energies are $E_0$ and $\mu_{phospca}(E_0)$ may represent a linear attenuation coefficient of calcium phosphate with respect to X-rays in which all photon energies are $E_0$. $L_{H_2O,i}$ (i=0, 1, 2, . . . ) may represent a thickness of water, wherein different i may correspond to different thicknesses of water. $L_{phospca,j}$ (j=0, 1, 2, . . . ) may represent a thickness of calcium phosphate, wherein different j may correspond to different thicknesses of calcium phosphate.

The hardening correction coefficient determination unit 740 may determine a hardening correction coefficient. In some embodiments, the hardening correction coefficient determination unit 740 may determine a hardening correction coefficient based on a thickness of water $L_{H_2O,i}$ (i=0, 1, 2, . . . ), a thickness of calcium phosphate $L_{phospcca,j}$ (j=0, 1, 2, . . . ), an ideal projection value ProjIdeal$_{i,j}$ of an object, and/or a hardening corrected projection value ProjCorrected$_{i,j}$ of the object.

In some embodiments, a channel may correspond to different objects. The hardening correction coefficient determination unit 740 may determine hardening corrected projection values ProjCorrected$_{i,j}$ of objects of various thicknesses and ideal projection values ProjIdeal$_{i,j}$ of objects of various thicknesses. The objects may be divided into one or more groups; thicknesses of water of objects belonging to a same group are the same and thicknesses of calcium phosphate are different (e.g., the thickness of calcium phosphate traverses a range); thicknesses of water of objects belonging to different groups are different. It should be understood that grouping the objects herein is performed for the convenience of describing differences among different objects in some embodiments.

For example, in a group including different objects corresponding to a channel, a thickness of water is 1 mm, a thickness of calcium phosphate may range from 0 to 200 mm. An increment for traversing the thickness range of calcium phosphate may be 1 mm, and the thicknesses of calcium phosphate may be 0, 1 mm, 2 mm, 3 mm, . . . , 200 mm. In some embodiments, the thickness range of calcium phosphate may be determined based on a thickness range of calcium phosphate in a tissue (e.g., a human tissue) of the scanning subject during scanning. The thickness range of calcium phosphate may be from 0 to 200 mm, from 0 to 400 mm, from 0 to 800 mm, from 100 to 200 mm, from 100 to 400 mm, no more than 200 mm, no more than 400 mm, no less than 50 mm, no less than 100 mm, etc. In some embodiments, the thickness range of calcium phosphate may be from 0 to 200 mm.

In some embodiments, the increment for traversing the thickness range of calcium phosphate may be, for example, a percentage of the thickness range of calcium phosphate such as, 1%, 2%, 3%, 4%, 5%, 6%, 8%, 10%, 12%, 15%, 20%, etc. During traversing the thickness range of calcium phosphate, the increment may be fixed or variable. For example, the increment may be 5% during traversing the thickness range of calcium phosphate. As another example, the increment may vary from 1% to 5% during traversing the thickness range of calcium phosphate. The hardening correction coefficient determination unit 740 may determine hardening corrected projection values of different objects and ideal projection values of different objects in the group. The hardening correction coefficient determination unit 740 may perform fitting on the parameters to obtain a hardening correction coefficient corresponding to the thickness (1 mm) of water in the channel. The parameters may include the thickness of water corresponding to the channel, the thicknesses of calcium phosphate corresponding to the channel, the hardening corrected projection values of the objects, and the ideal projection values of the objects.

The channel may correspond to different groups of objects. For example, different groups of objects may traverse a thickness range of water. For example, the thickness range of water may be from 0 to 500 mm. An increment for traversing the thickness range of water may be 1 mm, and the thicknesses of water may be 0, 1 mm, 2 mm, 3 mm, . . . , 500 mm. The hardening correction coefficient determination unit 740 may determine hardening correction coefficients corresponding to water of different thicknesses in a channel.

In some embodiments, the increment for traversing the thickness range of water may be a percentage of the thickness range of water, for example, 1%, 2%, 3%, 4%, 5%, 6%, 8%, 10%, 12%, 15%, 20%, etc. During traversing the thickness range of water, the increment may be fixed or variable. For example, the increment may be 5% during traversing the thickness range of water. As another example, the increment may vary from 1% to 5% during traversing the thickness range of water.

In some embodiments, the thickness range of water may be determined based on a thickness range of water in a tissue (e.g., a human tissue) of the scanning subject during scanning. For example, the thickness range of water may be from 0 to 200 mm, from 0 to 500 mm, from 0 to 800 mm, and from 0 to 1000 mm. In some embodiments, the thickness range of water may be from 0 to 500 mm.

The hardening correction coefficient determination unit 740 may determine hardening corrected projection values and ideal projection values of objects in different groups. The hardening correction coefficient determination unit 740 may perform a fitting to obtain hardening correction coefficients corresponding to a plurality of thicknesses (e.g., 1 mm, 2 mm, 4 mm) of water in the channel. The parameters may include the thicknesses of water corresponding to the channel, the thicknesses of calcium phosphate corresponding to the channel, the hardening corrected projection values of the objects, and the ideal projection values of the objects.

Figure 10:
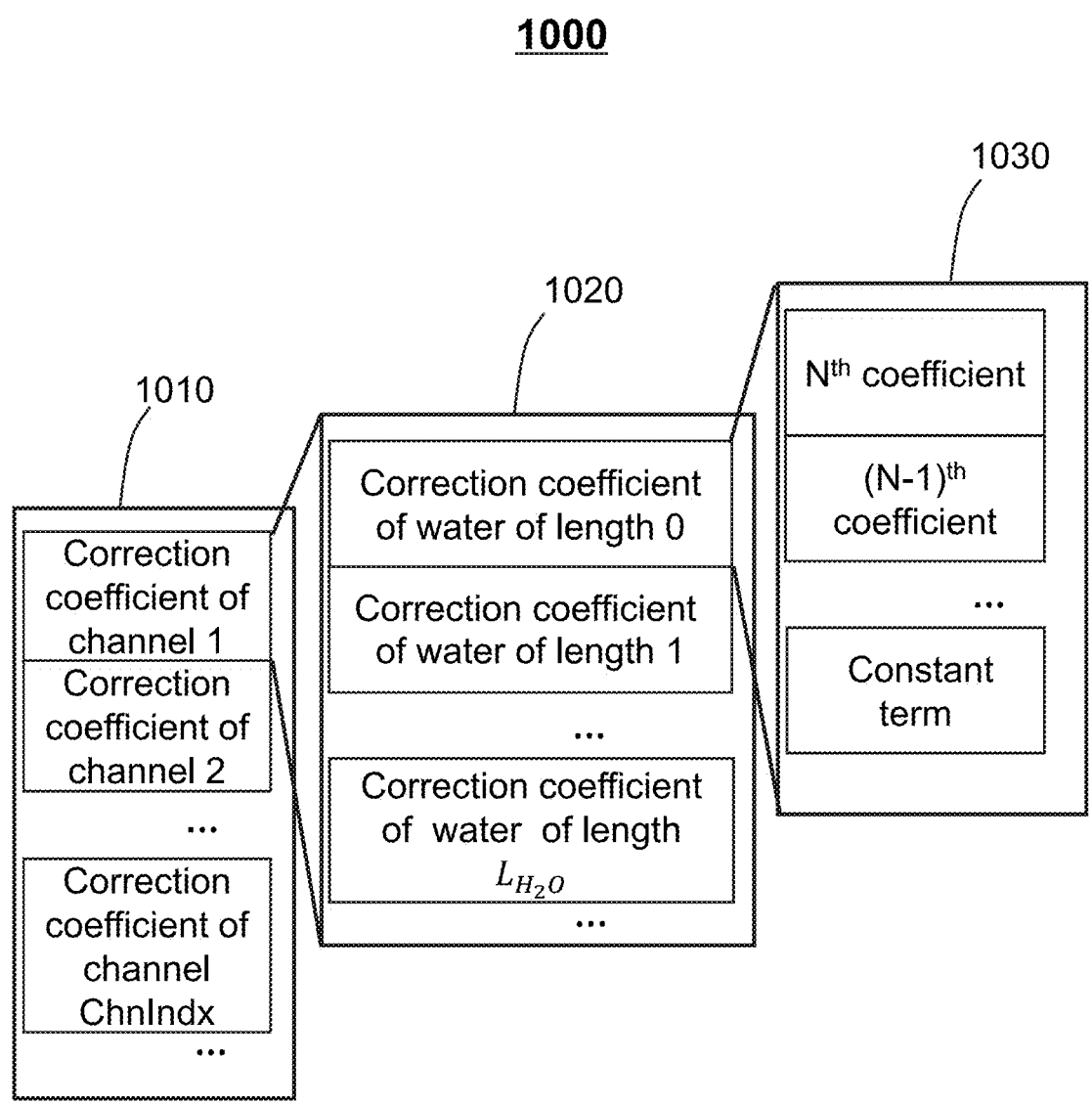
FIG. 10 is a structure diagram of a hardening correction coefficient database according to some embodiments of the present disclosure.

The hardening correction coefficient determination unit 740 may repeat the above operations for a plurality of channels, thereby generating data in the correction coefficient database shown in FIG. 10.

In some embodiments, the hardening correction coefficient determination unit 740 may perform a fitting to determine the hardening correction coefficient, wherein independent variables are the thickness of water $L_{H_2O,i}$ (i=0, 1, 2, . . . ) and the thickness of calcium phosphate $L_{phospca,j}$ (j=0, 1, 2, . . . ), and a dependent variable is a difference between the ideal projection value ProjIdeal$_{i,j}$ and the hardening corrected projection value ProjCorrected$_{i,j}$. In some embodiments, the fitting process may be performed according to the formula below:

$$\text{ProjError}_{i,j} = \text{ProjIdeal}_{i,j} - \text{ProjCorrected}_{i,j} = f(L_{H_2O,i}, L_{phospca,j}) \quad (5)$$

In formula (5), the function $f(L_{H_2O,i}, L_{phospca,j})$ may be a function of the thickness $L_{H_2O,i}$ (i=0, 1, 2, . . . ) of water and the thickness $L_{phospca,j}$ (j=0, 1, 2, . . . ) of calcium phosphate as independent variables. In some embodiments, the fitting may be a surface fitting. In some embodiments, the function $f(L_{H_2O,i}, L_{phospca,j})$ may be a surface function.

The hardening corrected projection value ProjCorrected$_{i,j}$ may vary with the thickness $L_{phospca,j}$ (j=0, 1, 2, . . . ) of calcium phosphate. In some embodiments, the hardening correction coefficient determination unit 740 may perform a fitting to determine the hardening correction coefficient, wherein the independent variable is the hardening corrected projection value ProjCorrected$_{i,j}$, and a dependent variable is a difference between the ideal projection value ProjIdeal$_{i,j}$ and the hardening corrected projection value Proj Corrected$_{i,j}$. In some embodiments, the fitting process may be performed according to the formula below:

$$\text{ProjError}_{i_0,j} = \text{ProjIdeal}_{i_0,j} - \text{ProjCorrected}_{i_0,j} = \sum_{k=0}^{N_2} \beta_k \cdot \text{ProjCorrected}_{i_0,j}^k \quad (6)$$

In formula (6), $i_0$ may represent that the thickness $L_{H_2O,i_0}$ of water is a fixed value, $N_2$ may be a polynomial order, and $\beta_k$ (k=0, 1, 2, . . . , $N_2$) may be a polynomial coefficient. In some embodiments, the fitting may be a polynomial fitting. The hardening correction coefficient determination unit 740 may determine corresponding hardening correction coefficients and generate a correction coefficient database. The correction coefficient database is described elsewhere in the present disclosure, for example, FIG. 10 and the description thereof.

In some embodiments, the value of $N_2$ may be an integer from 0 to 12. The value range of $N_2$ may be 0 to 3, 3 to 6, 6 to 9, 9 to 12, 0 to 6, 0 to 6, 6 to 12, no more than 10, no more than 12, no more than 15, no more than 20, no more than 25, no less than 3, no less than 5, no less than 8, no less than 10, no less than 12, no less than 15, no less than 20, etc. In some embodiments, the value of $N_2$ may be 2, 3, 4, 5, 6, 7, 8, etc.

Figure 8:
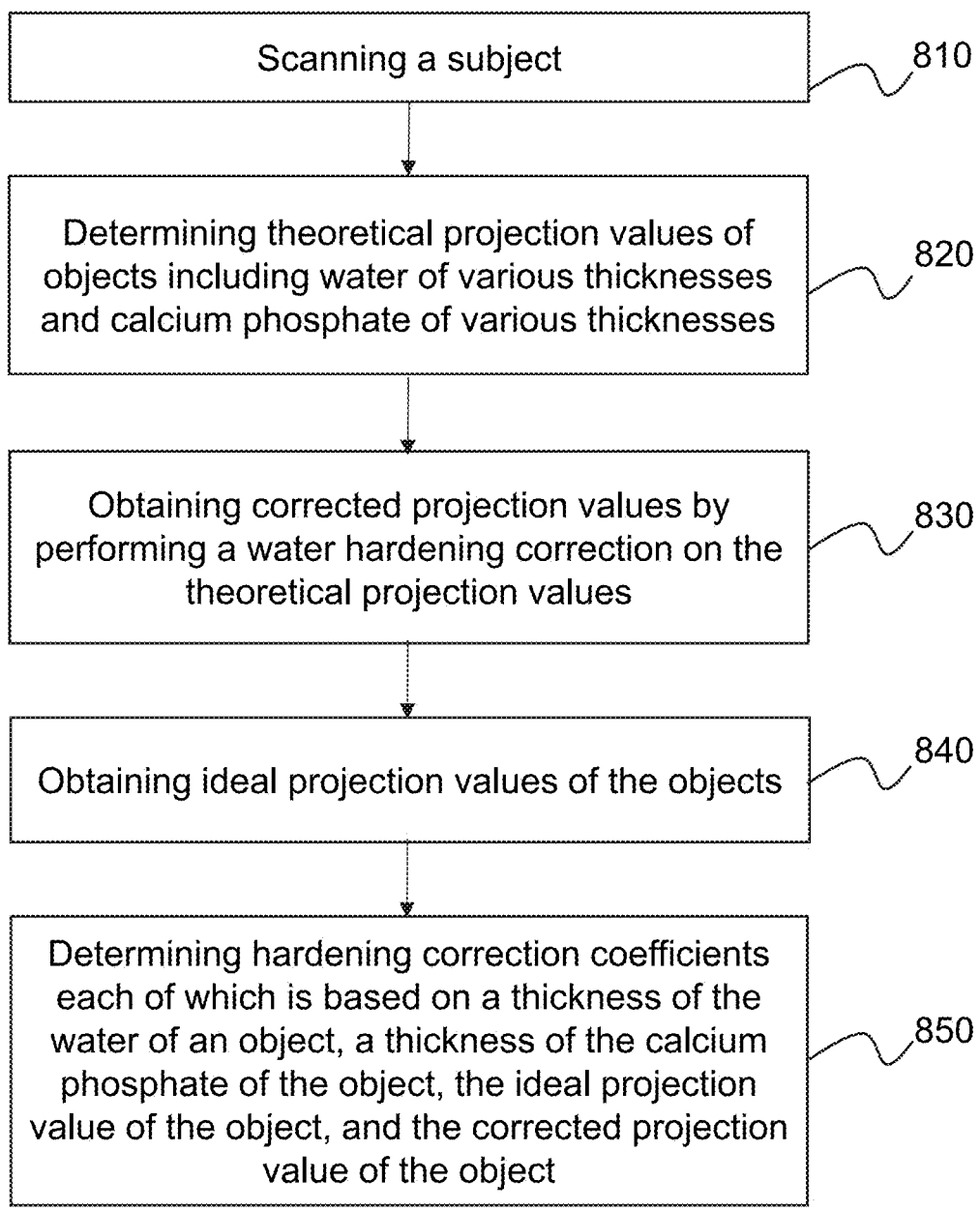
FIG. 8 is an exemplary flowchart of determining a hardening correction coefficient according to some embodiments of the present disclosure.

FIG. 8 is a schematic flowchart of determining a hardening correction coefficient according to some embodiments of the present disclosure. In 810, the imaging system 110 (e.g., the computerized tomography imaging system 200) may scan a scanning subject to obtain scanning data. The scanning subject may include a phantom. In some embodiments, a thickness and a material of the phantom may be known. In some embodiments, the phantom may be uniform. In some embodiments, the phantom may include a material similar to a human soft tissue. The material may be water or organic glass. In some embodiments, the objects may be divided into one or more groups; thicknesses of water of objects belonging to a same group are the same and thicknesses of calcium phosphate are different (e.g., the thicknesses of calcium phosphate traverse a range); thicknesses of water of objects belonging to different groups are different. It should be understood that grouping the objects herein is performed for the convenience of describing differences among different objects in some embodiments.

In 820, the processing device 120 may determine theoretical projection values ProjCal$_{i,j}$ of different objects. The object may include water and calcium phosphate. The theoretical projection values ProjCal$_{i,j}$ may be determined based on the scanning data acquired in 810 according to formula (3).

In 830, the processing device 120 may perform a water hardening correction on the theoretical projection values ProjCal$_{i,j}$ and determine water hardening correction coefficients corresponding to different thicknesses of water. In some embodiments, in 830, the processing device 120 may select the water hardening correction coefficient from the generated water hardening correction coefficients based on a thickness of water. The processing device 120 may further correct the theoretical projection values ProjCal$_{i,j}$ based on the selected water hardening correction coefficient and obtain hardening corrected projection values Proj Corrected$_{i,j}$. The water hardening correction is described elsewhere in the present disclosure, for example, FIG. 9A, FIG. 9B and the descriptions thereof.

In 840, the processing device 120 may determine ideal projection values ProjIdeal$_{i,j}$ of different objects. The object may include water and calcium phosphate. In 840, the processing device 120 may determine the ideal projection values ProjIdeal$_{i,j}$ according to formula (4).

In 850, the processing device 120 may generate hardening correction coefficients. In some embodiments, in 850, the processing device 120 may determine the hardening correction coefficients based on thicknesses of water L$_{H_2O,i}$ (i=0, 1, 2, . . . ), thicknesses of calcium phosphate L$_{phospca,j}$ (j=0, 1, 2, . . . ), ideal projection values ProjIdeal$_{i,j}$ of different objects, and/or water hardening corrected projection values of theoretical projection values of different objects (referred to as "hardening corrected projection value") Proj Corrected$_{i,j}$, and generate a correction coefficient database.

In some embodiments, the objects may be divided into one or more groups; thicknesses of water in objects belonging to a same group are the same, and thicknesses of calcium phosphate are different (e.g., the thicknesses of calcium phosphate traverse a range); thicknesses of water in objects belonging to different groups are different. It should be understood that grouping the objects herein is performed for the convenience of describing differences among different objects in some embodiments. As an example, the traversing of the thickness range of the calcium phosphate may be that selecting the thickness of the calcium phosphate as 0 mm, 1 mm, 2 mm, . . . , 200 mm, etc. In 850, the processing device 120 may determine hardening corrected projection values ProjCorrected$_{i,j}$ and ideal projection values ProjIdeal$_{i,j}$ of different objects. The processing device 120 may perform a fitting on the parameters to generate hardening correction coefficients. The parameters may include the thicknesses of water, the thicknesses of calcium phosphate, the hardening corrected projection values of the objects, and the ideal projection values of the objects. In some embodiments, the processing device 120 may determine the hardening correction coefficients according to formula (5). In some embodiments, the processing device 120 may determine the hardening correction coefficients according to formula (6). A correction coefficient database may be generated based on a plurality of hardening correction coefficients. The correction coefficient database is described elsewhere in the present disclosure, for example, FIG. 10 and the description thereof.

FIG. 9A is a schematic flowchart of generating a water hardening correction coefficient according to some embodiments of the present disclosure. In 910, the image processing system 120 may determine theoretical projection values of water of various thicknesses. In some embodiments, the theoretical projection values ProjCal$_{H_2O,i}$ of water may be determined according to the formula below:

$$ProjCal_{H_2O,i} = -\log\left(\frac{\int S(E)\cdot\exp[-\mu_{filter}(E)\cdot L_{filter}]\cdot \exp[-\mu_{H_2O}(E)\cdot L_{H_2O,i}]\cdot D(E)\cdot dE}{\int S(E)\cdot\exp[-\mu_{filter}(E)\cdot L_{filter}]\cdot D(E)\cdot dE}\right) \quad (7)$$

In formula (7), $\mu_{H_2O}(E)$ may represent a linear attenuation coefficient of water and L$_{H_2O,i}$ (i=0, 1, 2, . . . ) may represent a thickness of water. Different i may correspond to different thicknesses of water.

In 920, the processing device 120 may determine ideal projection values of water of various thicknesses. The ideal projection values ProjIdeal$_{H_2O,i}$ of water may be determined according to the formula below:

$$ProjIdeal_{H_2O,i} = \mu_{H_2O}(E_0)\cdot L_{H_2O,i} \quad (8)$$

In formula (8), $\mu_{H_2O}(E_0)$ may represent a linear attenuation coefficient of water with respect to X-rays in which all photon energies are E$_0$ and L$_{H_2O,i}$ (i=0, 1, 2, . . . ) may represent a thickness of water, wherein different i may correspond to different thicknesses of water.

In 930, the processing device 120 may perform fitting on ideal projection values ProjIdeal$_{H_2O,i}$ of water of various thicknesses and theoretical projection values ProjCal$_{H_2O,i}$ of water of various thicknesses, and determine water hardening correction coefficients. The water hardening correction coefficient $\alpha_k$ may be determined according to formula (9) below:

$$ProjIdeal_{H_2O,i} = \Sigma_{k=0}^{N_1}\alpha_k\cdot ProjCal_{H_2O,i}^k \quad (9)$$

In formula (9), N$_1$ may be a polynomial order and $\alpha_k$ (k=0, 1, 2, . . . , N$_1$) may be a water hardening correction coefficient. In some embodiments, the value of N$_1$ may be an integer from 0 to 100. The value range of N$_1$ may be 0 to 5, 5 to 10, 10 to 15, 15 to 20, 20 to 25, no more than 10, no more than 12, no more than 15, no more than 20, no more than 25, no less than 3, no less than 5, no less than 8, no less than 10, no less than 12, no less than 15, no less than 20, etc. In some embodiments, the value of N$_1$ may be 2, 3, 4, 5, 6, 7, 8, etc.

FIG. 9B is a schematic flowchart of performing a water hardening correction based on a water hardening correction coefficient according to some embodiments of the present disclosure. In 940, the processing device 120 may select a water hardening correction coefficient $\alpha_k$ based on a channel. The water hardening correction coefficients $\alpha_k$ corresponding to water of various thicknesses may be determined according to formula (9).

In 960, the processing device 120 may correct the theoretical projection values ProjCal$_{i,j}$ of objects of various thicknesses based on the selected water hardening correction coefficient $\alpha_k$. The hardening corrected projection values ProjCorrected$_{i,j}$ may be determined according to the formula below:

$$ProjCorrected_{i,j} = \Sigma_{k=0}^{N_1}\alpha_k\cdot ProjCal_{i,j}^k \quad (10)$$

In formula (10), $\alpha_k$ may be a water hardening correction coefficient selected by the processing device 120 in 940 based on the thickness of water.

FIG. 10 is a structure diagram of a correction coefficient database according to some embodiments of the present disclosure. The correction coefficient database may be stored in the form of a table in the correction module 430 of the processing device 120. The correction coefficient database may store hardening correction coefficients of different objects. According to the descriptions described elsewhere in the present disclosure, a hardening correction coefficient reflects a relationship between an original projection value and an ideal projection value. In some embodiments, a hardening corrected projection value of the theoretical projection value obtained based on the water hardening correction may be close to the original projection value. The original projection value may be a projection value obtained by performing an orthographic projection of the reference image. Data in the hardening correction coefficient database may be generated by the hardening correction coefficient determination unit 740.

A first layer 1010 in the correction coefficient database may store data of channel index numbers. The channel index number is described elsewhere in the present disclosure, for example, FIG. 13 and the description thereof. A second layer 1020 in the correction coefficient database may store thicknesses of water. The second layer 1020 may store a plurality of groups of thicknesses of water. Each group of thicknesses of water corresponds to different objects corresponding to a channel index number. A third layer 1030 of the correction coefficient database may store correction coefficients. A thickness of water may correspond to a group of correction coefficients. The correction coefficients may be polynomial coefficients obtained based on a fitting process according to formula (6).

It should be noted that the determination of the correction coefficient is not limited to the fitting process according to formula (6). The correction coefficient is not limited to the polynomial coefficient. The correction coefficient may be obtained based on other fitting methods. The correction coefficient may be a coefficient of other forms.

The processing device 120 may determine a channel index number. The processing device 120 may determine a thickness of water in an object corresponding to the channel index number. The processing device 120 may determine a correction coefficient based on the channel index number and the corresponding thickness of water. The thickness of water may correspond to the length of water described in FIG. 10.

In some embodiments, the second layer 1020 in the correction coefficient database may store thicknesses of calcium phosphate. The third layer 1030 of the correction coefficient database may store correction coefficients corresponding to the thicknesses of calcium phosphate. The processing device 120 may determine a channel index number. The processing device 120 may determine a thickness of calcium phosphate in an object corresponding to the channel index number. The processing device 120 may determine a correction coefficient based on the channel index number and the corresponding thickness of calcium phosphate.

Figure 11:
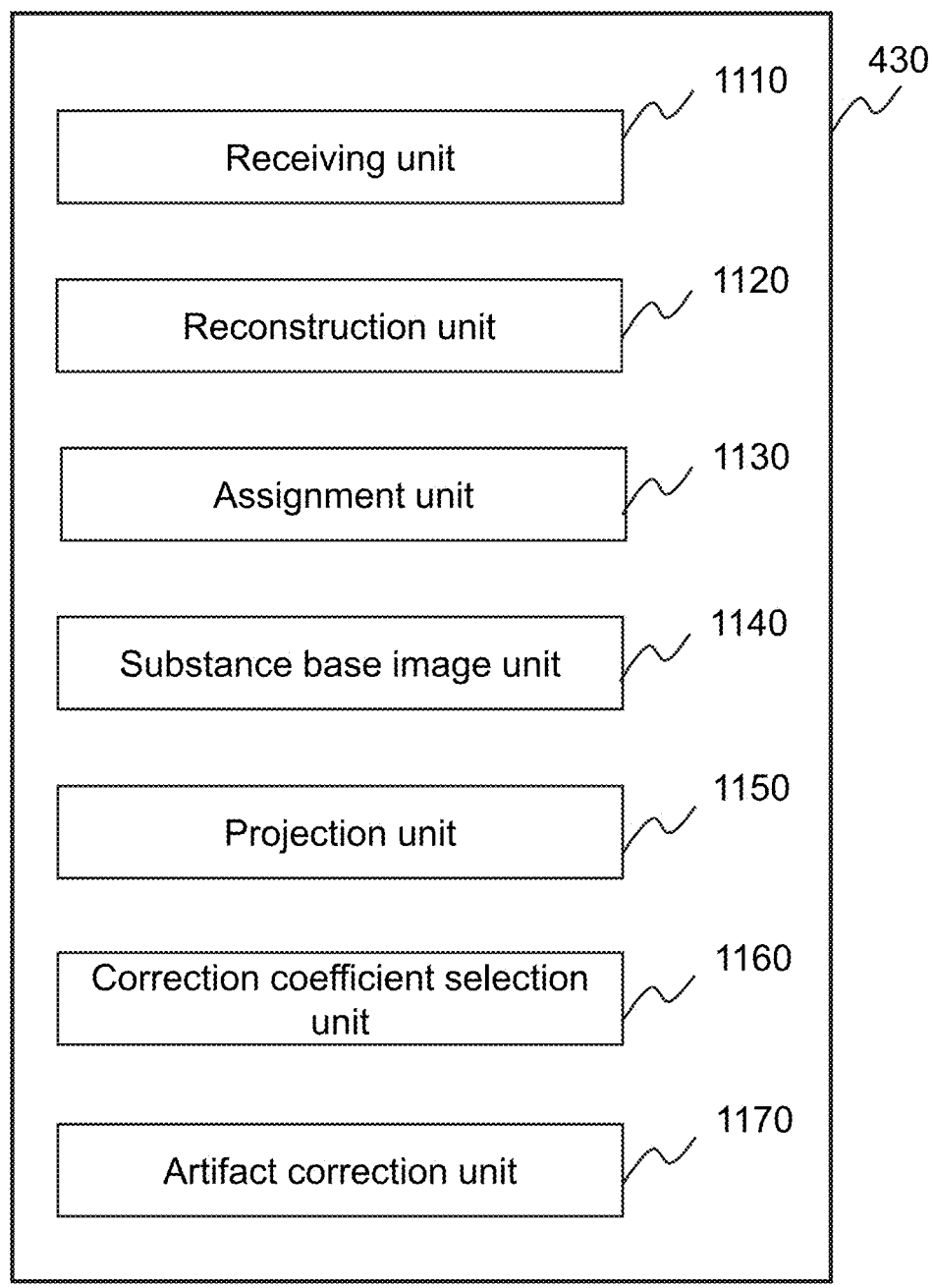
FIG. 11 is a schematic diagram of a correction module 430 in the processing device 120 according to some embodiments of the present disclosure.

FIG. 11 is a schematic diagram of a correction module 430 in the processing device 120 according to some embodiments of the present disclosure. The correction module 430 may include the following units: a receiving unit 1110, a reconstruction unit 1120, an assignment unit 1130, a substance base image unit 1140, a projection unit 1150, a correction coefficient selection unit 1160, and an artifact correction unit 1170. It should be noted that the above description of the structure of the correction module 430 in the processing device 120 is only exemplary and is not intended to limit the present disclosure to the scope of the embodiment. In some embodiments, the correction module 430 may also include other units. In some embodiments, some of the above units may be unnecessary. In some embodiments, some of the above units may be combined into a single unit for cooperation. In some embodiments, the above units may be independent. "The units may be independent" may refer to that each unit executes a respective function. In some embodiments, the above units may be interrelated. "The units may be interrelated" may refer to that data in each unit may be cross used.

The receiving unit 1110 may receive scanning data of a scanning subject in the imaging system 110 (e.g., the computerized tomography imaging system 200). The scanning data may be obtained by directly scanning the subject by the imaging system 110 or by accessing the stored scanning data of the subject. The subject may include a patient. The scanning data may be stored in the processing device 120.

The reconstruction unit 1120 may perform a reconstruction according to a first field of view based on the scanning data to obtain an original image including artifact(s), that is, the image to be corrected. The first field of view may be set by a user (e.g., a doctor, etc.). In some embodiments, the artifact may be a bone sclerosis artifact. The reconstruction unit 1120 may perform a re-reconstruction according to a second field of view based on the scanning data to obtain a reference image of the image to be corrected. The second field of view may be larger than or equal to the first field of view (e.g., a field of view set by a user). The second field of view may be set to ensure that the reference image includes all scanned portions of the scanning subject in the first field of view.

The assignment unit 1130 may determine a water proportion for a pixel of the reference image. In some embodiments, the assignment unit 1130 may determine the water proportion for the pixel according to a tissue type of the pixel and a CT value of the pixel. The tissue type of a pixel may be determined based on a segmentation of the reference image.

In some embodiments, the processing device 120 may determine the tissue type of a pixel based on one or more segmentation methods. In some embodiments, the segmentation method may include a threshold segmentation. The tissue type may be a human tissue, a bone tissue, a soft tissue, a head support/bed plate, etc. The assignment unit 1130 may reduce the water proportion for the pixel as the CT value of the pixel increases.

For example, the bone tissue may be approximated as a mixture of water and calcium phosphate according to a certain proportion. The higher the CT value of the bone tissue is, the lower the water proportion determined by the assignment unit 1130 may be, and the higher the proportion of calcium phosphate determined by the assignment unit 1130 may be. For example, a CT value of a pixel of the bone tissue is 10, a water proportion determined by the assignment unit 1130 may be 5%. A CT value of a pixel of the bone tissue is 20, and the water proportion determined by the assignment unit 1130 may be 10% or 15%.

The substance base image unit 1140 may obtain a water base image of the reference image by multiplying the CT value of a pixel in the reference image by the water proportion. The water proportion may be assigned by the assignment unit 1130.

The projection unit 1150 may perform an orthographic projection of the water base image and the reference image to obtain an equivalent length of water corresponding to a projection line. In some embodiments, the projection unit 1150 may perform an orthographic projection operation of the water base image and the reference image at a channel number which is less than or equal to a channel number at which the reference image is reconstructed and a projection angle which is less than or equal to and a projection angle at which the reference image is reconstructed. The channel number and the projection angle are described elsewhere in the present disclosure, for example, FIG. 13 and the description thereof. The projection unit 1150 may determine a projection value of water ProjWater and an original projection value ProjOrig of water along the orthographic projection line. In some embodiments, the channel number and the projection angle of the orthographic projection may be rotated based on the principle that no obfuscation artifact occurs in an image reconstructed based on a subsequent back projection.

Figure 13:
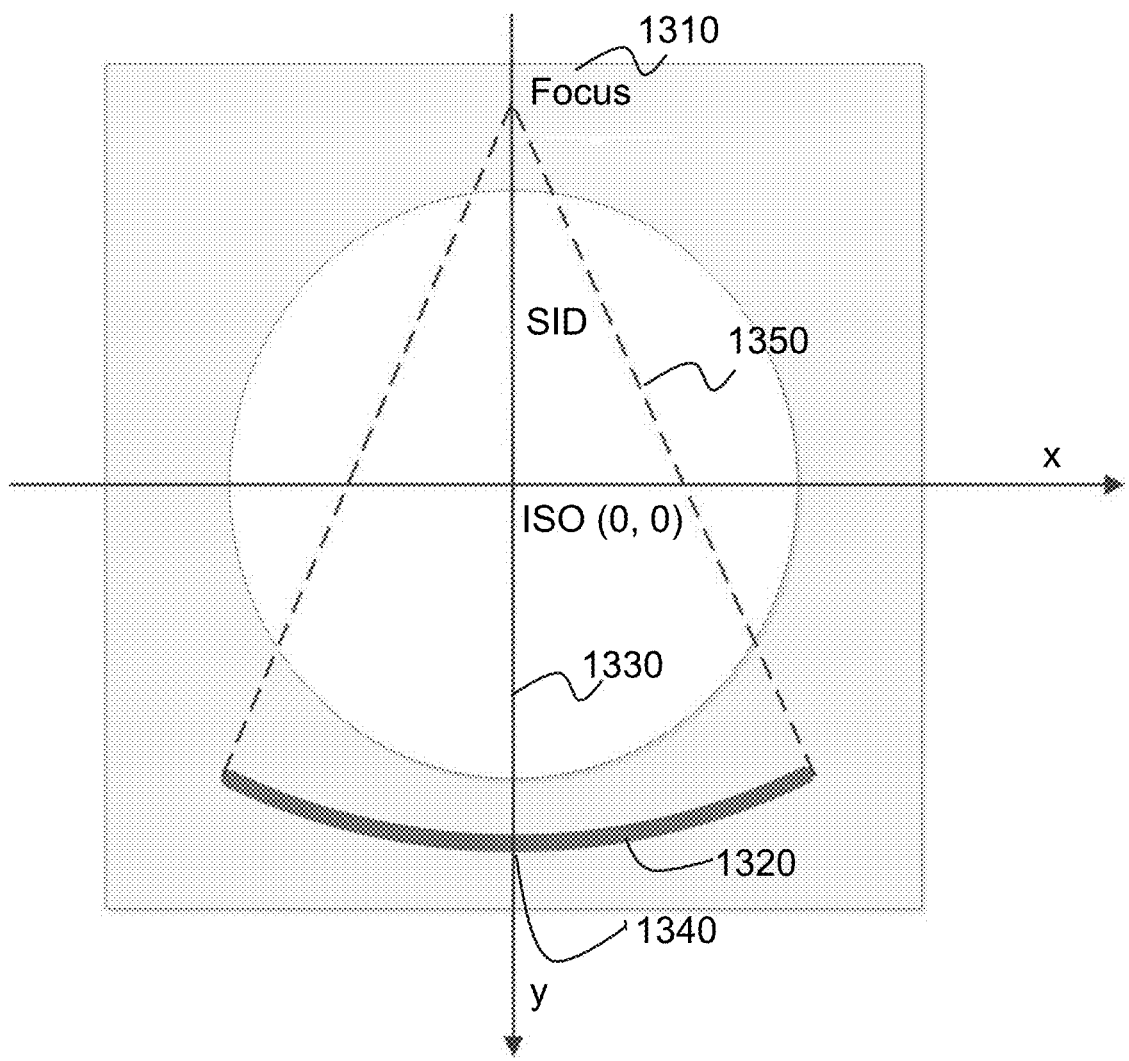
FIG. 13 is a spatial schematic diagram of projection lines according to some embodiments of the present disclosure.

The projection unit 1150 may determine a channel index number corresponding to an orthographic projection line. The projection unit 1150 may determine an equivalent length of water along the orthographic projection line. In an x-y coordinate system (as shown in FIG. 13), an equation of an orthographic projection line may be expressed as:

$$A \cdot x + B \cdot y + C = 0 \tag{11A}$$

In formula (11A), A, B, and C may be coefficients in a general expression of a linear equation, respectively. A distance from a rotation center (ISO) of the CT gantry to the projection line may be expressed as $$D = \frac{|C|}{\sqrt{A^2 + B^2}} \tag{11B}$$

The channels corresponding to the projection line are:

$$ChnIndx1 = ChnIndex_{middle} - \arcsin\left(\frac{D}{SID}\right) / \left(\frac{ChnWidth}{SID}\right) \tag{12}$$

and $$ChnIndx2 = ChnIndex_{middle} + \arcsin\left(\frac{D}{SID}\right) / \left(\frac{ChnWidth}{SID}\right) \tag{13}$$

In formula (12) and formula (13), $ChnIndex_{middle}$ may be a central channel index number, SID may be a distance from a focus of the CT gantry to the rotation center (ISO), and ChnWidth may be an average width of the detector unit (i.e., the channel). Since a filtration of the CT gantry is almost symmetrical with respect to the center channel, the projection unit 1150 may select ChnIndx1 or ChnIndx2 as the channel index number ChnIndx corresponding to the orthographic projection line.

In some embodiments, the projection unit 1150 may determine the equivalent length of water according to the formula below:

$$L_{H_2O} = \frac{ProjWater}{CTNum_{H_2O}} \tag{14}$$

In formula (14), $L_{H_2O}$ may be the equivalent length of water, ProjWater may be a projection value of water along the direction of the projection line, and $CTNum_{fir}$ may be a CT value of water under an assumption that a CT value of air is 0. An equivalent length of water corresponding to an orthographic projection line may be a ratio of a projection value of the water base image corresponding to the projection line to a CT value of water which the projection line traverses. In some embodiments, an equivalent length of a substance corresponding to an orthographic projection line may be a ratio of a projection value of a base image of the substance corresponding to the projection line to a CT value of the substance which the projection line traverses.

The correction coefficient selection unit 1160 may select a hardening correction coefficient from the correction coefficient database shown in FIG. 10 based on the channel index number ChnIndx and the equivalent length of water $L_{fir}$. The equivalent length of water may correspond to the length of water described in FIG. 10.

The artifact correction unit 1170 may perform an artifact correction on the image to be corrected based on the selected hardening correction coefficient. In some embodiments, the artifact correction unit 1170 may obtain modified projection data based on the selected hardening correction coefficient and the original projection value ProjOrig of the reference image. For example, the modified projection data may be obtained according to the formula below:

$$ProjCorrected = \sum_{k=0}^{N_3} \beta_k \cdot ProjOrig^k \tag{15}$$

In formula (15), $N_3$ may be a polynomial order. In some embodiments, the value of $N_3$ may be an integer from 0 to 12. The value range of $N_3$ may be 0 to 3, 3 to 6, 6 to 9, 9 to 12, 0 to 6, 0 to 9, 6 to 12, no more than 10, no more than 12, no more than 15, no more than 20, no more than 25, no less than 3, no less than 5, no less than 8, no less than 10, no less than 12, no less than 15, no less than 20, etc. In some embodiments, the value of $N_3$ may be 2, 3, 4, 5, 6, 7, 8, etc. In some embodiments, the value of $N_3$ may be equal to the value of $N_2$ in formula (6).

In formula (15), the output ProjCorrected of the polynomial may be modified projection data obtained by multiplying the original projection values of the orthographic projection line of the reference image by the corresponding hardening correction coefficients and accumulating the results. The artifact correction unit 1170 may perform a back projection reconstruction of the modified projection data ProjCorrected according to the first field of view to obtain an image including artifact(s). The artifact correction unit 1170 may remove the image including artifact(s) from the image to be corrected to obtain a corrected image, realizing an artifact correction.

Figure 12:
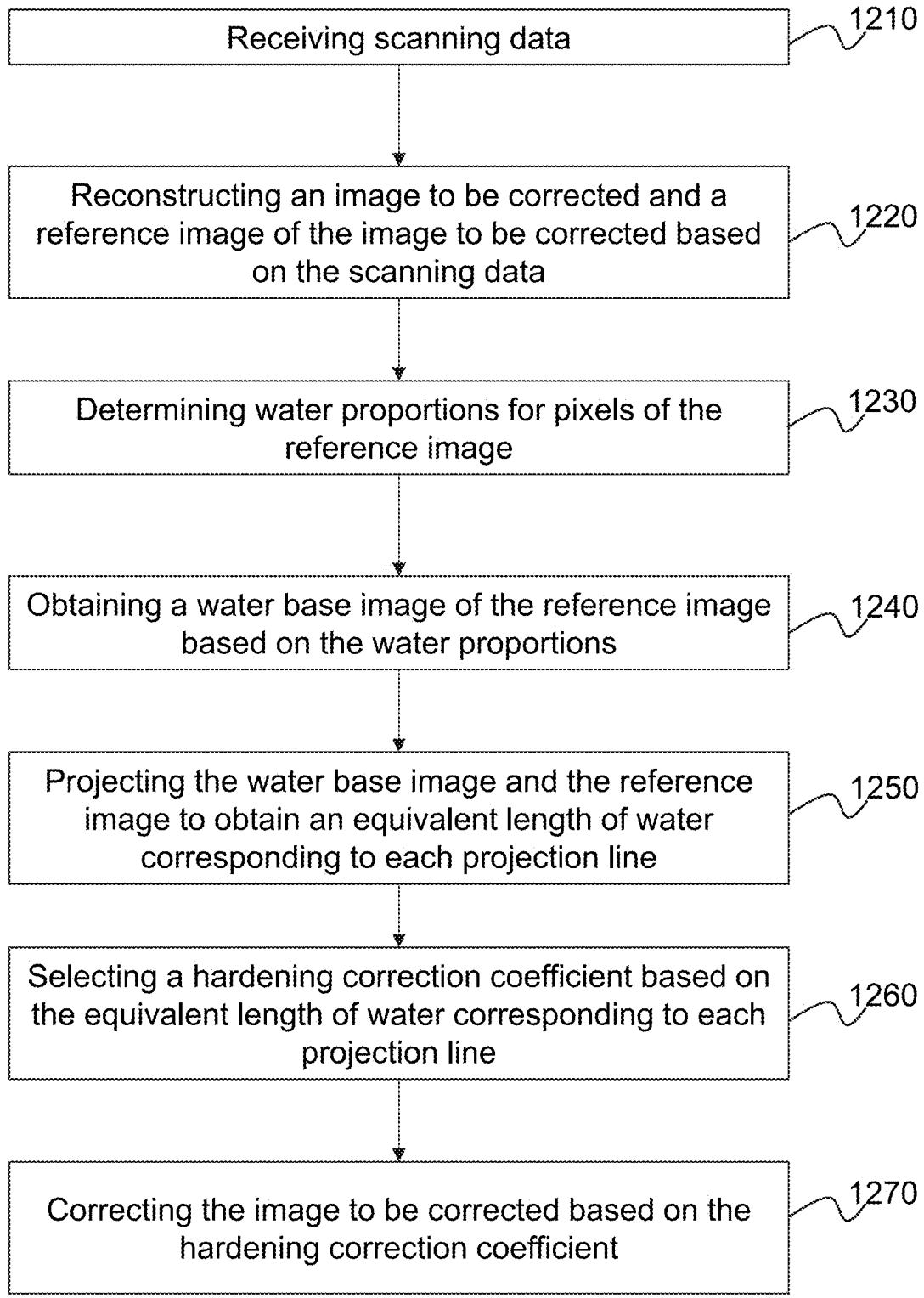
FIG. 12 is an exemplary flowchart of performing an artifact correction according to some embodiments of the present disclosure.

FIG. 12 is a schematic flowchart of performing an artifact correction according to some embodiments of the present disclosure. In 1210, the processing device 120 (the computerized tomography imaging system 200) may acquire scanning data. The scanning data may be scanning data obtained by scanning a subject by the imaging system 110 or stored scanning data of the subject. The scanning subject may include a patient. The scanning data may be stored in the processing device 120.

In 1220, the processing device 120 may reconstruct an image to be corrected and a reference image of the image to be corrected based on the scanning data. In some embodiments, in 1220, the processing device 120 may perform a reconstruction to obtain an original image including artifact(s) (i.e., the image to be corrected) based on the scanning data according to the first field of view. In some embodiments, the artifact may be a bone sclerosis artifact. In 1220, the processing device 120 may perform a re-reconstruction to obtain the reference image of the image to be corrected based on the scanning data according to the second field of view.

In 1230, the processing device 120 may determine water proportions for pixels of the reference image. In some embodiments, the processing device 120 may determine water proportions for the pixels according to tissue types of the pixels and CT values of the pixels. The tissue type of a pixel may be determined based on a segmentation of the reference image. The processing device 120 may reduce the water proportion for a pixel as a CT value of the pixel increases.

In 1240, the processing system 120 may obtain a water base image of the reference image based on the water proportions. The water base image of the reference image may be obtained by multiplying the CT value of a pixel of the reference image by the water proportion.

In 1250, the processing device 120 may perform a projection operation of the water base image and the reference image. The processing device 120 may obtain an equivalent length of water corresponding to an orthographic projection line based on the projection operation. In some embodiments, the channel index number ChnIndx corresponding to the orthographic projection line may be determined according to formula (11), formula (12), and formula (13). In some embodiments, the equivalent length $L_{H_2O}$ of water corresponding to the orthographic projection line may be determined according to formula (14).

In 1260, the processing device 120 may select a hardening correction coefficient. The processing device 120 may select the hardening correction coefficient from the correction coefficient database shown in FIG. 10 based on the channel index number ChnIndx and the equivalent length of water $L_{H_2O}$. The equivalent length of water may correspond to the length of water described in FIG. 10.

In 1270, the processing device 120 may perform an artifact correction on the image to be corrected based on the selected hardening correction coefficient. In some embodiments, the processing device 120 may determine modified projection data according to formula (15). The processing device 120 may perform a back projection reconstruction of the modified projection data according to the first field of view to obtain an image including artifact(s). The processing device 120 may remove the image including artifact(s) from the image to be corrected to obtain a corrected image, realizing an artifact correction.

FIG. 13 is a spatial schematic diagram of projection lines according to some embodiments of the present disclosure. The ISO may be the rotation center of the CT gantry. In some embodiments, the rotation center ISO may be fixed. In the x-y coordinate system, the ISO may be at the origin. SID may be a distance from a focus 1310 to the rotation center ISO. An intersection of a detection unit 1320 and the y-axis may be located at a point 1340. The length of a line connecting the focus 1310 and the point 1340 may be the central channel index number $ChnIndex_{middle}$. In some embodiments, an angle between the line connecting the rotation center ISO and the focus and the negative direction of the y axis may be the projection angle. The projection angle may be non-negative. In FIG. 13, the focus is on the y axis, the line connecting the rotation center ISO and the focus coincides with the y axis, and the projection angle is zero. In some embodiments, the focus may deviate from the original position when the detection unit 1320 rotates around the rotation center ISO. There may be an angle between the line connecting the rotation center ISO and the focus and the y axis. The line connecting the rotation center ISO and the focus forms different projection angles with the y axis.

A shape (e.g., a fan shape) 1350 formed by the focus 1310 and the detection unit 1320 may include one or more channels. A channel may be a channel (e.g., a fan channel) formed by the focus 1310 and a portion of the detection unit 1320. Adjacent channels may be connected with each other. In some embodiments, the arrangement of channels in the detection unit 1320 may be M rows by N columns. A section of the detection unit 1320 shown in FIG. 13 may include a row of channels. In some embodiments, the number of channels in a row may range from 0 to 5000. In some embodiments, the number of channels in a row may range from 0 to 100, 100 to 200, 200 to 300, 300 to 400, 400 to 500, 500 to 600, 600 to 700, 700 to 800, 800 to 900, 900 to 1000, 1000 to 2000, 2000 to 3000, 3000 to 4000, 4000 to 5000, etc. In some embodiments, the number of channels in a row may range from 800 to 850. In some embodiments, the number of channels in a column may range from 0 to 400. In some embodiments, the number of channels in a column may be no more than 50, no more than 100, no more than 150, no more than 200, no more than 250, no more than 300, no more than 350, no more than 400, etc. In some embodiments, the number of channels in a column may be no more than 350.

In some embodiments, a length of an arc of the detection unit corresponding to a channel may range from 0.1 mm to 10.0 mm. In some embodiments, the length of the arc corresponding to a channel may range from 0.1 mm to 0.2 mm, 0.2 mm to 0.3 mm, 0.3 mm to 0.4 mm, 0.4 mm to 0.5 mm, 0.5 mm to 0.6 mm, 0.6 mm to 0.7 mm, 0.7 mm to 0.8 mm, 0.8 mm to 0.9 mm, 0.9 mm to 1.0 mm, 1.0 mm to 2.0 mm, 2.0 mm to 3.0 mm, 3.0 mm to 4.0 mm, 4.0 mm to 5.0 mm, 5.0 mm to 6.0 mm, 6.0 mm to 7.0 mm, 7.0 mm to 8.0 mm, 8.0 mm to 9.0 mm, 9.0 mm to 10.0 mm, etc. In some embodiments, the length of the arc corresponding to a channel may be 0.1 mm. The lengths of arcs corresponding to different channels may be the same or different.

In some embodiments, a field angle of the detection unit 1320 to the focus 1310 may range from 0 to 100 degrees. In some embodiments, the field angle may range from 0.1 degree to 1.0 degree, 1.0 degree to 2.0 degrees, 2.0 degrees to 3.0 degrees, 3.0 degrees to 4.0 degrees, 4.0 degrees to 5.0 degrees, 5.0 degrees to 6.0 degrees, 6.0 degrees to 7.0 degrees, 7.0 degrees to 8.0 degrees, 8.0 degrees to 9.0 degrees, 9.0 degrees to 10.0 degrees, 10.0 degrees to 20.0 degrees, 20. degrees to 30.0 degrees, 30.0 degrees to 40.0 degrees, 40.0 degrees to 50.0 degrees, 50.0 degrees to 60.0 degrees, 60.0 degrees to 70.0 degrees, 70.0 degrees to 80.0 degrees, 80.0 degrees to 90.0 degrees, 90.0 degrees to 100.0 degrees, etc. In some embodiments, the field angle may be 53 degrees or 54 degrees.

Figure 14A:
FIG. 14A is a schematic diagram of an image to be corrected according to some embodiments of the present disclosure.
Figure 14B:
FIG. 14B is a schematic diagram of a reference image of the image to be corrected according to some embodiments of the present disclosure.
Figure 14C:
FIG. 14C is a schematic diagram of a water base image of the reference image according to some embodiments of the present disclosure.
Figure 14D:
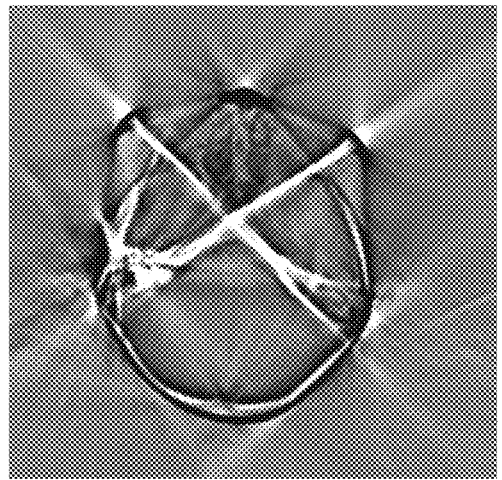
FIG. 14D is a schematic diagram of an image including artifact(s) according to some embodiments of the present disclosure.
Figure 14E:
FIG. 14E is a schematic diagram of a corrected image according to some embodiments of the present disclosure.

FIG. 14A is a schematic diagram of an image to be corrected according to some embodiments of the present disclosure. FIG. 14B is a schematic diagram of a reference image of the image to be corrected according to some embodiments of the present disclosure. FIG. 14C is a schematic diagram of a water base image of the reference image according to some embodiments of the present disclosure. FIG. 14D is a schematic diagram of an image including artifact(s) according to some embodiments of the present disclosure. FIG. 14E is a schematic diagram of a corrected image according to some embodiments of the present disclosure. The corrected image may be obtained by removing the image including artifact(s) (FIG. 14D) from the image to be corrected (FIG. 14A).

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by the present disclosure, and are within the spirit and scope of the exemplary embodiments of the present disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "data block," "module," "engine," "unit," "component," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, radio frequency (RF), or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to surface modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present disclosure are not limited to that precisely as shown and described.

I claim:

1. A computerized tomography artifact correction method, executed by at least one machine, wherein each of the at least one machine includes at least one processor and a storage device, comprising:
receiving scanning data;
reconstructing an image to be corrected and a reference image of the image to be corrected based on the scanning data;
determining proportions of a first substance for pixels of the reference image;
obtaining a base image of the first substance based on the proportions of the first substance;
performing a projection of the base image of the first substance and the reference image along a plurality of projection lines;
for each of the plurality of projection lines:
obtaining an equivalent length of the first substance corresponding to the projection line; and
selecting a hardening correction coefficient based on the equivalent length of the first substance corresponding to the projection line; and
performing an artifact correction on the image to be corrected based on the hardening correction coefficients.

2. The method of claim 1, wherein the image to be corrected is an image including a bone sclerosis artifact.

3. The method of claim 1, further comprising:
reconstructing the image to be corrected based on a first field of view; and
reconstructing the reference image based on a second field of view, wherein the second field of view is larger than or equal to the first field of view.

4. The method of claim 1, further comprising:
determining a first pixel and a tissue type of the first pixel based on the reference image; and
determining the proportion of the first substance for the first pixel based on the tissue type and a CT value of the first pixel.

5. The method of claim 4, wherein the proportion of the first substance for the first pixel reduces as the CT value of the first pixel increases.

6. The method of claim 4, further comprising:
determining a proportion of a second substance for the first pixel.

7. The method of claim 6, wherein,
the tissue type is bone tissue;
the first substance is water; and
the second substance is calcium phosphate.

8. The method of claim 1, wherein
the projection of the base image of the first substance and the reference image is performed according to a second channel number and a second projection angle, and wherein,
the reference image is reconstructed according to a first channel number and a first projection angle;
the second channel number is less than the first channel number; and
the second projection angle is less than the first projection angle.

9. The method of claim 1, further comprising:
selecting the hardening correction coefficient from a correction coefficient database based on the equivalent length of the first substance.

10. The method of claim 1, wherein the equivalent length of the first substance is a ratio of a projection value of the base image of the first substance corresponding to the projection line to a CT value of the first substance which the projection line traverses.

11. The method of claim 1, the performing the artifact correction on the image to be corrected based on the hardening correction coefficients comprising:
obtaining original projection data of the reference image based on the projection;
determining modified projection data based on the original projection data and the hardening correction coefficients;
obtaining an artifact image based on the modified projection data; and
subtracting the artifact image from the image to be corrected.

12. An artifact correction method, executed by at least one machine, wherein each of the at least one machine includes at least one processor and a storage device, comprising:
determining a bone tissue as an object including a first substance and a second substance;
obtaining a theoretical projection value of the bone tissue;
performing a hardening correction with respect to the first substance on the theoretical projection value of the bone tissue to obtain a corrected projection value;
determining an ideal projection value of the bone tissue; and
determining a hardening correction coefficient based on a thickness of the second substance, the ideal projection value of the bone tissue, and the corrected projection value.

13. The method of claim 12, the obtaining the theoretical projection value of the bone tissue and the determining the ideal projection value of the bone tissue comprising:
obtaining scanning data of a phantom.

14. The method of claim 13, further comprising:
obtaining an equivalent filtration thickness corresponding to a channel through which a measured projection value of the phantom is equal to the theoretical projection value.

15. The method of claim 13, wherein the phantom comprises water or organic glass.

16. The method of claim 12, the performing the hardening correction with respect to the first substance on the theoretical projection value comprising:
determining theoretical projection values and ideal projection values of the first substance of various thicknesses;
determining hardening correction coefficients with respect to the first substance by fitting the theoretical projection values and the ideal projection values;
selecting a hardening correction coefficient with respect to the first substance based on a thickness of the first substance; and
correcting the theoretical projection value of the bone tissue based on the hardening correction coefficient with respect to the first substance.

17. The method of claim 12, the determining a hardening correction coefficient comprising:
performing fitting, wherein an independent variable is a thickness of the second substance, and a dependent variable is a difference between the ideal projection value and the corrected projection value; and obtaining the hardening correction coefficient based on the fitting.

18. The method of claim 12, the determining a hardening correction coefficient comprising:

performing fitting, wherein independent variables are the thickness of the first substance and the thickness of the second substance, and a dependent variable is a difference between the ideal projection value and the corrected projection value; and obtaining the hardening correction coefficient based on the fitting.

19. The method of claim 12, wherein the first substance is water and the second substance is calcium phosphate.

20. A system comprising:

at least one processor; and information, when the information executed by at least one processor, cause the at least one processor to effectuate a method comprising:

receiving scanning data;

reconstructing an image to be corrected and a reference image of the image to be corrected based on the scanning data;

determining proportions of a first substance for pixels of the reference image;

obtaining a base image of the first substance based on the proportions of the first substance;

performing a projection of the base image of the first substance and the reference image along a plurality of projection lines;

for each of the plurality of projection lines:

obtaining an equivalent length of the first substance corresponding to the projection line; and selecting a hardening correction coefficient based on the equivalent length of the first substance corresponding to the projection line; and performing an artifact correction on the image to be corrected based on the hardening correction coefficients.

* * * * *